United States Patent [19]

Bretting et al.

[11] Patent Number: 5,446,034
[45] Date of Patent: Aug. 29, 1995

[54] VITAMIN D ANALOGUES

[75] Inventors: Claus Aage S. Bretting, Frederiksberg; Gunnar Grue-Sørensen, Ølstykke, both of Denmark

[73] Assignee: Leo Pharmaceuitcal Products Ltd. A/S (Lovens Kemiske Fabrik Produktionsaktiesel SKAB), Ballerup, Denmark

[21] Appl. No.: 211,420
[22] PCT Filed: Mar. 23, 1993
[86] PCT No.: PCT/DK93/00105
  § 371 Date: Apr. 4, 1994
  § 102(e) Date: Apr. 4, 1994
[87] PCT Pub. No.: WO93/19044
  PCT Pub. Date: Sep. 30, 1993

[30] Foreign Application Priority Data

Mar. 26, 1992 [GB] United Kingdom ............... 9206648

[51] Int. Cl.⁶ .............................................. C07C 401/00
[52] U.S. Cl. ...................................... 514/167; 552/653
[58] Field of Search ........................ 552/653; 514/167

[56] References Cited

FOREIGN PATENT DOCUMENTS

WOA9203414 3/1992 WIPO .

*Primary Examiner*—Johann Richter
*Assistant Examiner*—Kimberly J. Kestler
*Attorney, Agent, or Firm*—Cushman Darby & Cushman

[57] ABSTRACT

The invention relates to compounds of formula I in which formula X is hydrogen or hydroxy; $R^1$ and $R^2$ stand for hydrogen or a $C_1-C_6$ hydrocarbyl radical; or taken together with the carbon atom bearing the group X, can form a $C_3-C_8$ carbocyclic ring; $R^3$ stands for hydrogen or a $C_1-C_{10}$ hydrocarbyl radical or for $YR^4$, in which Y stands for the radicals —CO—, —CO—O—, —CO—S—, —CS—, —CS—O—, —C-S—S—, —SO— or $SO_2$—, and $R^4$ stands for hydrogen or a $C_1-C_{10}$ hydrocarbyl radical; Q is a single bond or a $C_1-C_8$ hydrocarbylene diradical. $R^1,R^2,R^3$ and/or Q may be optionally substituted with one or more deuterium or fluorine atoms. The compounds show an antiinflammatory and immunomodulating effect as well as stong activity in inducing differentiation and inhibiting undesirable proliferation of certain cells.

8 Claims, No Drawings

VITAMIN D ANALOGUES

This application is a 371 of PCT/DK93/00105.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, and a number of disease states including diabetes mellitus, hypertension, acne, alopecia, skin ageing, imbalance in the immune system, inflammatory diseases such as rheumatoid arthritis and asthma as well as diseases characterized by abnormal cell differentiation and/or cell proliferation such as e.g. psoriasis and cancer, and for promoting osteogenesis and treating osteoporosis.

The compounds of the invention constitute a novel class of vitamin D analogues and are represented by the general formula I

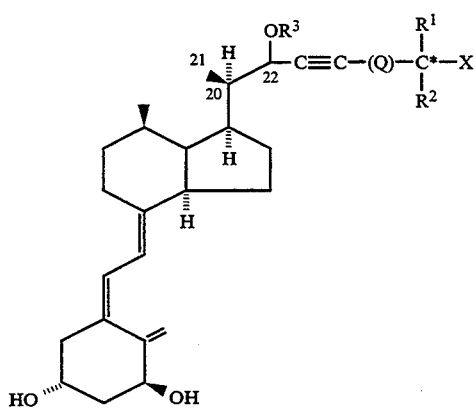

in which formula X is hydrogen or hydroxy; $R^1$ and $R^2$, which may be the same or different, stand for hydrogen or a $C_1$–$C_6$ hydrocarbyl radical; or $R^1$ and $R^2$ taken together with the carbon atom (starred in formula I) bearing the group X, can form a $C_3$–$C_8$ carbocyclic ring; $R^3$ stands for hydrogen or a $C_1$–$C_{10}$ hydrocarbyl radical or for $YR^4$ in which Y stands for the radicals —CO—, —CO—O—, —CO—S—, —CS—, —C-S—O—, —CS—S—, —SO— or —SO$_2$—, and $R^4$ stands for hydrogen or a $C_1$–$C_{10}$ hydrocarbyl radical; Q is a single bond or a $C_1$–$C_8$ hydrocarbylene diradical. $R^1$, $R^2$, $R^3$ and/or Q may be optionally substituted with one or more deuterium or fluorine atoms.

In the context of this invention, the expression hydrocarbyl radical (hydrocarbylene diradical) indicates the residue after removal of 1 (2) hydrogen atom(s) from a straight, branched or cyclic saturated or unsaturated hydrocarbon.

Examples of $R^1$ and $R^2$ when taken separately include (apart from hydrogen), but are not limited to, methyl, trifluoromethyl, ethyl, vinyl, normal-, iso- and cyclopropyl, and 1-methylvinyl.

Examples of $R^1$ and $R^2$ when taken together include di-, tri-, tetra- and penta-methylene.

Examples of $R^3$ and $R^4$ include (apart from hydrogen), but are not limited to, methyl, trifluoromethyl, ethyl, propyl, normal-, iso- and cyclopropyl, normal-, iso-, sec-, and tert-butyl, normal- and iso-pentyl, phenyl and benzyl.

Examples of Q include a single bond, methylene, di-, tri- and tetra-methylene, —CH$_2$—CH=CH—, —CH$_2$—C≡C—, —CH=CH—CH$_2$—, —C≡C—CH$_2$—, phenylene (C$_6$H$_4$; ortho, meta, para), —CH$_2$—(C$_6$H$_4$)- (ortho, meta, para), and —(C$_6$H$_4$)—CH$_2$— (ortho, meta, para).

As can be seen from formula I, depending on the meanings of $R^1$, $R^2$, $R^3$, Q and X the compounds of the invention can comprise several diastereoisomeric forms (e.g. R or S configuration at the starred carbon atom). The invention covers all these diastereoisomers in pure form as well as mixtures of diastereoisomers.

In particular, both diastereoisomers having the two possible configurations at the carbon atom marked "22" are included. These are referred to as isomer A and isomer B.

In addition, prodrugs of I in which one or more of the hydroxy Groups are masked as Groups which can be reconverted to hydroxy groups in vivo are also within the scope of the invention.

Compounds of formula I in which X is hydrogen also may act as prodrugs, as these compounds are relatively inactive in vitro, but are converted to active compounds of formula I by enzymatic hydroxylation after administration to the patient.

It has recently been shown that 1α,25-dihydroxyvitamin D$_3$ (1,25(OH)$_2$D$_3$) influences the effects and/or production of interleukins (Muller, K. et al, Immunol. Lett. 17, 361–366 (1988)), indicating the potential use of this compound in the treatment of diseases characterized by a dysfunction of the immune system, e.g. autoimmune diseases, AIDS, host versus Graft reactions, and rejection of transplants or other conditions characterized by an abnormal interleukin-1 production, e.g. inflammatory diseases such as rheumatoid arthritis and asthma.

It has also been shown that 1,25(OH)$_2$D$_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25(OH)$_2$D$_3$, or its pro-drug 1α—O—H—D$_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for 1,25(OH)$_2$D$_3$ is suggested by the recent observation of an association between hereditary vitamin D resistance and alopecia: treatment with 1,25(OH)$_2$D$_3$ may promote hair growth (Editorial, Lancet, March 4, 1989, p. 478). Also, the fact that topical application of 1,25(OH)$_2$D$_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of 1,25(OH)$_2$D$_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, MC 903, containing a 22,23-double bond, a 24-hydroxy group and in which the carbon atoms 25, 26 and 27 are incorporated in a three membered ring, is a potent inducer of cell differentiation and inhibitor of cell proliferation which shows only moderate activity on calcium metabolism in vivo (Binderup, L. and Bramm, E., Blochem. Pharmacol. 37, 889–895 (1988)). However, this selectivity is not paralleled by in vitro studies, which show that MC 903 binds equally well as $1,25(OH)_2D_3$ to the intestinal vitamin D receptor. Possibly, the low in vivo activity on calcium metabolism of MC 903 is due to a rapid metabolism of the compound, thus limiting the potential of this compound for systemic use.

24-Homo-1,25-dihydroxyvitamin $D_3$ and 26-homo-1,25-dihydroxyvitamin $D_3$ (together with their 22,23-didehydroanalogues) (Ostrem, V. K.; Tanaka, Y.; Prahl, J.; DeLuca, H. F.; and Ikekawa, N.; Proc. Natl. Acad. Sci. USA 84, 2610–14 (1987)) have been claimed to have the same binding affinity as $1,25(OH)_2D_3$ to both the rat and chicken intestinal receptor and the receptor in a human myeloid leukemia cell line (HL-60), and yet to be 10-fold more potent than $1,25(OH)_2D_3$ in inducing differentiation of HL-60 cells in vitro. In vivo, these compounds are respectively "significantly less potent" and "more potent" than $1,25(OH)_2D_3$ in calcium metabolism assessments.

26,27-Dimethyl-1α,25-dihydroxyvitamin $D_3$ has been synthesized, but the published information regarding its biological activities is contradictory. (Sai, H.; Takatsuto, S.; Hara, N.; and Ikekawa, N.; Chem. Pharm. Bull. 33, 878–881 (1985) and Ikekawa, N.; Eguchi, T.; Hara, N.; Takatsuto, S.; Honda, A.; Mori, Y.; and Otomo, S.; Chem. Pharm. Bull. 35, 4362–4365 (1987)). The closely related 26,27-diethyl-1α,25-dihydroxyvitamin $D_3$ is also reported by these authors; in this case as having "almost no vitamin D activity" (i.e. calcium metabolism effects) while being 10-fold more potent than $1,25(OH)_2D_3$ in inducing cell differentiation.

U.S. Pat. No. 4,804,502 discloses compounds containing a triple bond in the side chain of Vitamin D, and these compounds are claimed to be useful in the treatment of disease states characterized by metabolic calcium deficiencies.

The fact that there are only small structural differences between the compounds of the prior art referred to above indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

The compounds of the present invention differ structurally from the above vitamin D analogues, some of which have been reported to have potent effects on cell differentiation/proliferation in the configuration of the methyl group at carbon-20. This "unnatural" configuration present in the compounds I (and also in compounds according to our previous international patent application number PCT/DK90/00156, filing date 19th June, 1990, publication number WO 91/00271, and international patent application number PCT/DK91/00200, filing date 11th July, 1991, publication number WO 92/03414), has surprisingly been found to have a profound and advantageous biological significance. Thus a particular compound of formula I, when compared to the corresponding compound containing the "natural" C-20 configuration (methyl and hydrogen radicals exchanged), is observed to show one or more of the following advantages:

(a) more potent effects on cell differentiation/proliferation
(b) a greater selectivity in favour of the potent effects on cell differentiation/proliferation contra the effects on calcium metabolism;
(c) more potent effects on the production and action of interleukins;
(d) a greater selectivity in favour of the effects on interleukin production and action contra the effects on calcium metabolism.

The compounds of the invention are therefore especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g. in autoimmune diseases, including diabetes mellitus, host versus graft reaction, and rejection of transplants; and additionally for the treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin ageing, including photo-ageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis. For these indications the presently described compounds have a higher therapeutic ratio than the prior art compounds (see U.S. Pat. No. 4,948,789 and EP 0385446 A2).

The present compounds may be used in combination with other pharmaceuticals. In the prevention of graft rejection and graft versus host reaction, a treatment with the present compounds may advantageously be combined with e.g. a cyclosporin treatment.

Compounds I can be prepared from the vitamin D-derived aldehyde compound 1 (Scheme 1); a synthesis of which has been reported [M. J. Calverley, Tetrahedron 43, 4609 (1987)], for example by the routes outlined in Scheme 1.

The following standard abbreviations are used throughout this disclosure: Me=methyl; Et=ethyl; Bu=n-butyl; i-Pen=isopentyl; Ph=phenyl; Bn=benzyl; Ac=acetyl; Piv=pivaloyl; THP=tetrahydro-4H-pyran-2-yl; TMS =trimethylsilyl; DMAP=4-dimethylaminopyridine; PPTS=pyridinium p-toluenesulfonate; pet.ether=petroleum ether; THF=tetrahydrofuran; TBAF=tetra-(n-butyl)-ammonium fluoride; b.p.=boiling point; PLC=preparative thin-layer chromatography.

Scheme 1
Synthesis of Compounds I of the Invention

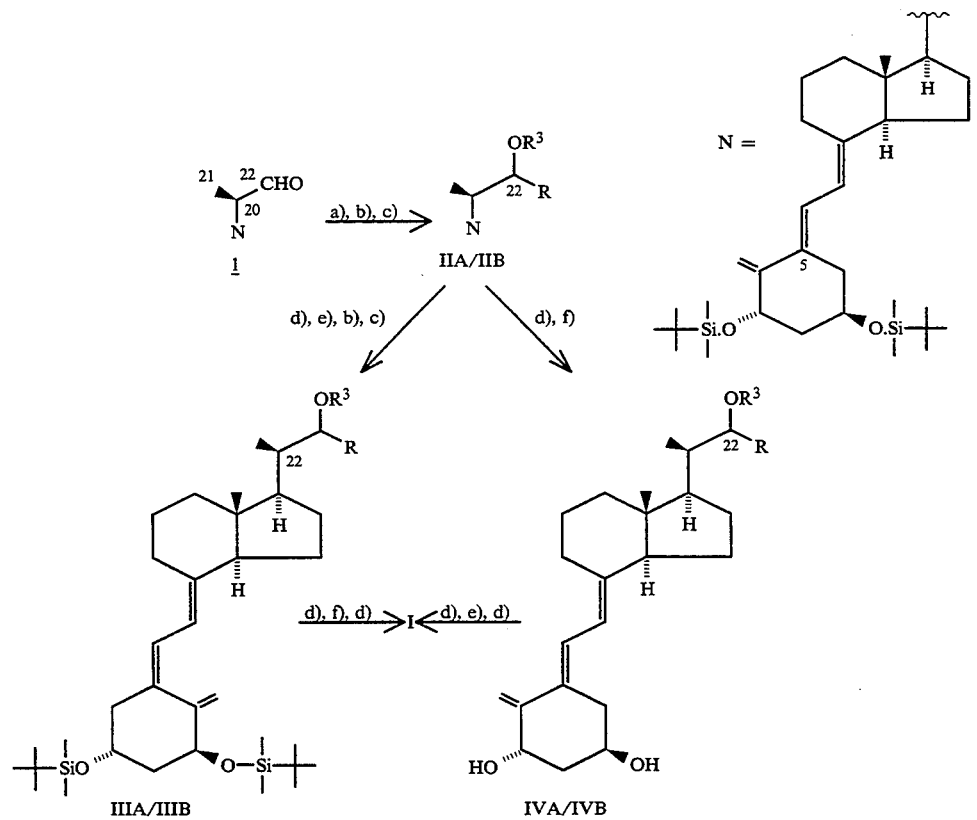

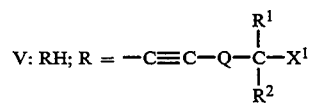

$X^1$ = H, OH, $OR^5$
$R^5$ = alcohol protective group, e.g. tri (loweraklyl)-silyl or THP
$R^1$, $R^2$, $R^3$ and Q have the above meanings.

Notes to Scheme 1 a) (i) Compound 1 is reacted with the anion $R^-$, derived from the side chain building block, RH, of general formula V, with a suitable base.
   (ii) The resulting mixture of the two C-22-epimers, IIA and IIB ($R^3$ = H), is separated.
b) Optional alkylation of the C-22-hydroxy compounds ($R^3$ = H) of type II or III to the corresponding compound II or III, where $R^3$ = $C_1$-$C_{10}$ hydrocarbyl.
c) Optional acylation of the C-22-hydroxy compound ($R^3$ = H) of type II or III to the corresponding compound II or III, where $R^3$ = $YR^4$; Y and $R^4$ having the above meanings.
d) Optional functional group modification in the side chain.
e) Isomerization of Compounds II or IV to the corresponding compound III or I, by means of UV-light in the presence of a triplet sensitizer, e.g. anthracene.
f) Deprotection of Compounds II or III to the corresponding compound IV or I, e.g. by HF or by TBAF followed by PPTS.

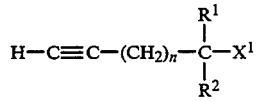

The side chain building blocks RH of general formula V are either known compounds, or they can be prepared by standard methods known to the specialist.

In particular, this applies to the side chain building blocks RH necessary for the preparation of the exemplified compounds (101–149). The procedures according to Scheme 1 can be used analogously to the specific preparations and examples mentioned in the following.

As a nonlimiting illustration, the preparation of some compounds of the general formula V where $Q=(CH_2)_n$, $X^1=OR^5$ and $R^5=-Si(CH_3)_3$ or THP (n=0-3) is outlined in Scheme 2, but similar compounds of formula V with other Q and/or $X_1$ may be prepared by analogous methods. Some specific side chain building blocks RH are listed in Table 1 and their syntheses are described in the preparations.

Scheme 2
Synthesis of some Side Chain Building Blocks V

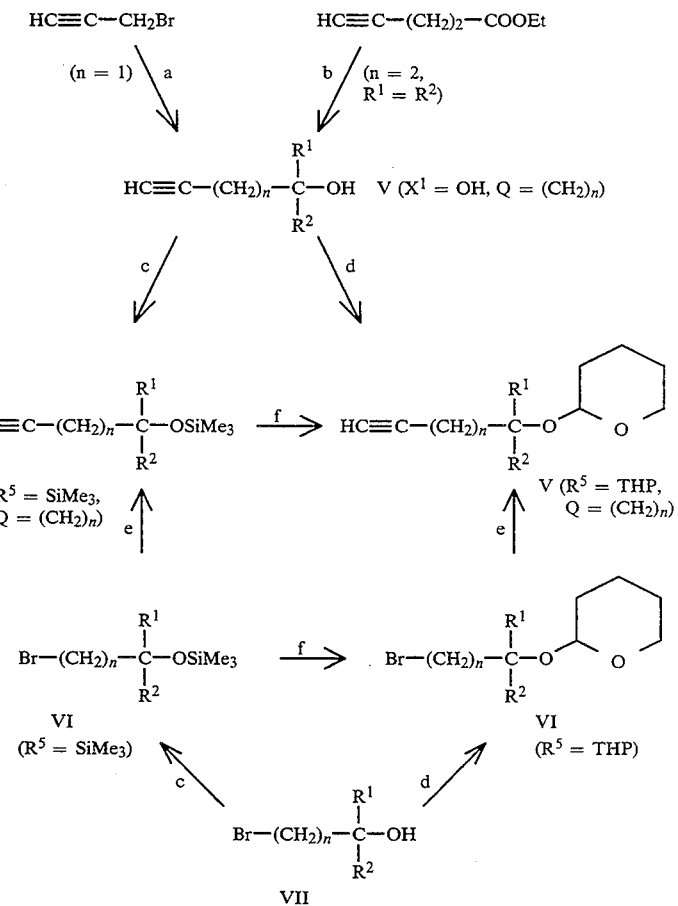

Notes to Scheme 2 a. (i) Al, (ii) $R^1R^2C=O$;

b. Grignard reagent $R^1MgBr$ or $R^1MgI$;

c. $Me_3SiCl$/base;

d. dihydropyran/acid;

e. acetylene/Na/liq.$NH_3$;

f. (i) MeOH/acid, (ii) dihydropyran/acid.

TABLE 1

Some Side Chain Building Blocks, RH of General Formula V
$(Q = (CH_2)_n, n = 0-3, R^1 = R^2 = CH_3$ or $C_2H_5; R^5 = SiMe_3$ or THP)

| Prep. Number | Compound Number | General Procedure | RH |
|---|---|---|---|
| 1 | 2 | 1 | H—≡—⟨—OSi⟨ |
| 2 | 3 | 2 | H—≡—⟨—O—⟨O⟩ |

TABLE 1-continued

Some Side Chain Building Blocks, RH of General Formula V
(Q = (CH$_2$)$_n$, n = 0-3, R$^1$ = R$^2$ = CH$_3$ or C$_2$H$_5$; R$^5$ = SiMe$_3$ or THP)

| Prep. Number | Compound Number | General Procedure | RH |
|---|---|---|---|
| 4 | 5 | 2 | |
| 6 | 7 | 2 | |
| 8 | 9 | 2 | |
| 10 | 11 | 6 | |

Intermediates for the preparation of the side chain building blocks, RH of Table 1, are either known compounds or can e.g. be prepared from the compounds listed in Table 2. The syntheses of these compounds are described in the Preparations.

C-22-epimers, here designated IIA and/IB. It is usually preferable to separate the IIA and IIB epimers which can conveniently be done by chromatography.

Nonlimiting illustrations of such compounds of formula IX (R$^3$=H) are given in Table 3. In this table these

TABLE 2

Some Intermediaties for the Synthesis of the RH (V) of Table 1

| Type | Prep. No. | Compound No. | General Procedure | Formula |
|---|---|---|---|---|
| VI | 3 | 4 | 3 | |
| VI | 5 | 6 | 4 | |
| VI | 7 | 8 | 4 | |
| VII | 9 | 10 | 5 | |

The reaction of the aldehyde 1 with the side chain building blocks, RH=H—C≡C—Q—C(R1)(R2)OR$^5$, can be performed by standard methods of nucleophilic addition of acetylenic anions (R$^-$) to carbonyl compounds; i.e. by treating the RH with a suitable base, such as n-BuLi, in a suitable anhydrous solvent, such as THF, then adding 1, to give II (R$^3$=H) after usual aqueous work-up (which is normally implied in all the reactions of Schemes I and II). In general the reaction product II (R$^3$=H) is a mixture of the two possible compounds are described as separate 22-epimers IIA or IIB (preparations 11, 12, 13, 21, 22 and 23). The compounds IIA are chromatographically less polar than the corresponding IIB epimers (see general procedure 7), and usually the IIA epimers are formed in higher yields than the corresponding IIB epimers. Furthermore, there is usually a difference in the chemical shift of the $^1$H-NMR signals of the C-21 methyl group which in the IIA epimers occur in the range of circa δ 1.04–1.02 (d, 3H), whereas for the IIB epimers the corresponding signals are found at slightly higher field (circa δ 1.00–0.97).

The optional alkylation or acylation of the C-22-hydroxy compounds ($R^3$=H) of general formula II or III to yield the corresponding compound where $R^3$ is $C_1$-$C_{10}$ hydrocarbyl or $YR^4$ can be performed by standard methods well known to the specialist. Illustrative, but non limiting, compounds of this sort are listed in Table 3. Table 3 also contains the other examples of photoisomerized compounds of general formula III along with references to the preparation of each compound.

In the alkylation reaction use is preferably made of an alkylating agent $R^3Z$, in which Z stands for a good leaving group, such as for example Cl—, Br—, I—, $CH_3SO_3$—, p—$CH_3$—$C_6H_4$—$SO_3$— or $CF_3SO_3$—; the R3Z being allowed to react with the anion of the appropriate compound II or III ($R^3$=H), derived therefrom by means of a suitable strong base, such as an alkali-metal alkoxide, alkyl alkali-metal or alkali-metal hydride. A useful method is described in General Procedure 8, and in more detail in the included preparations; a suitable crown ether may be added as a phase transfer agent to accelerate the alkylation process.

In the alkylation reaction producing compounds II or III where $R^3$=$YR^4$, use may advantageously be made of standard acylation procedures, such as reaction of the alcohol (II or III, $R^3$=H) with an acid chloride or acid anhydride ($R^4YCl$ or ($R^4Y)_2O$), or by forming the acylating agent in situ from the corresponding acid $R^4YOH$ and a dehydrating or condensing agent, such as e.g. a carbodiimide or an assisting acid anhydride, forming an intermediary mixed anhydride.

Furthermore, the addition of a suitable base, such as a tertiary amine, may often be profitably applied during the acylation; in many cases addition of a special heterocyclic amine like DMAP may accelerate the acylation process considerably. Examples of acylation procedures are given in General Procedure 9 and illustrated in more detail in the included preparations.

Exemplified Compounds I of the invention are listed in Table 4, the numbered examples giving reference to illustrative methods of synthesis, together with spectroscopic data for those same compounds of the examples.

It should be noted that the preparations and examples of Schemes 1 and 2 are illustrative only, the particular synthesis of each step and the order in which each step is performed can be varied greatly. Furthermore, the radical R: —C≡C—Q—C($R^1$)($R^2$)($X^1$) may optionally be a radical which can be converted to this at any convenient later stage (or over several stages). Thus R in compounds II, III and IV does not necessarily have the same meaning along a particular synthetic sequence. The conversion of R to —C≡C—Q—C($R^1$)($R^2$)$X^1$ may well involve several steps and possibly involve a temporary protection of the sensitive triene system of the molecule. Apart from any necessary modification of $R^3$ or within the side chain (R), the conversion of II to I involves a photoisomerisation step and a deprotection step, analogous to the steps used in the last stages of the synthesis of other vitamin D analogues (see European patent No. 0 227 836).

TABLE 3

Intermediates of formulas II and III; Q = $(CH_2)_n$

| Type (See Scheme 1) | Preparation Number | Compound Number | General Procedure | $R^3$ | n | $R^1$ | $R^2$ | $X^1$ |
|---|---|---|---|---|---|---|---|---|
| IIA | 11 | 12 | 7 | H | 0 | Et | Et | $OSiMe_3$ |
| IIB | 11 | 13 | 7 | H | 0 | Et | Et | $OSiMe_3$ |
| IIA | 12 | 14 | 7 | H | 1 | Me | Me | OTHP |
| IIA | 13 | 15 | 7 | H | 1 | Et | Et | OTHP |
| IIB | 13 | 16 | 7 | H | 1 | Et | Et | OTHP |
| IIA | 14 | 17 | 8 | Me | 1 | Et | Et | OTHP |
| IIA | 15 | 18 | 8 | Et | 1 | Et | Et | OTHP |
| IIA | 16 | 19 | 8 | Bu | 1 | Et | Et | OTHP |
| IIA | 17 | 20 | 8 | i-Pen | 1 | Et | Et | OTHP |
| IIA | 18 | 21 | 8 | Bn | 1 | Et | Et | OTHP |
| IIA | 19 | 22 | 9 | Ac | 1 | Et | Et | OTHP |
| IIA | 20 | 23 | 9 | Piv | 1 | Et | Et | OTHP |
| IIA | 21 | 24 | 7 | H | 2 | Me | Me | OTHP |
| IIB | 21 | 25 | 7 | H | 2 | Me | Me | OTHP |
| IIA | 22 | 26 | 7 | H | 2 | Et | Et | OTHP |
| IIB | 22 | 27 | 7 | H | 2 | Et | Et | OTHP |
| IIA | 23 | 28 | 7 | H | 3 | Et | Et | OTHP |
| IIB | 23 | 29 | 7 | H | 3 | Et | Et | OTHP |
| IIIA | 24 | 30 | 10 | H | 0 | Et | Et | $OSiMe_3$ |
| IIIB | 25 | 31 | 10 | H | 0 | Et | Et | $OSiMe_3$ |
| IIIA | 26 | 32 | 9 | Ac | 0 | Et | Et | $OSiMe_3$ |
| IIIA | 27 | 33 | 9 | C(S)OPh | 0 | Et | Et | $OSiMe_3$ |
| IIIA | 28 | 34 | 10 | H | 1 | Me | Me | OTHP |
| IIIA | 29 | 35 | 10 | H | 1 | Et | Et | OTHP |
| IIIB | 30 | 36 | 10 | H | 1 | Et | Et | OTHP |
| IIIA | 31 | 37 | 10 | Me | 1 | Et | Et | OTHP |

| Type (See Scheme 1) | Prepar- No. | Compound Number | General Procedure | $R^3$ | n | $R^1$ | $R^2$ | X |
|---|---|---|---|---|---|---|---|---|
| IIIA | 32 | 38 | 10 | Et | 1 | Et | Et | OTHP |
| IIIA | 33 | 39 | 10 | Bu | 1 | Et | Et | OTHP |
| IIIA | 34 | 40 | 10 | i-Pen | 1 | Et | Et | OTHP |
| IIIA | 35 | 41 | 10 | Bn | 1 | Et | Et | OTHP |
| IIIA | 36 | 42 | 10 | Ac | 1 | Et | Et | OTHP |
| IIIA | 37 | 43 | 10 | Piv | 1 | Et | Et | OTHP |
| IIIA | 38 | 44 | 10 | H | 2 | Me | Me | OTHP |
| IIIB | 39 | 45 | 10 | H | 2 | Me | Me | OTHP |
| IIIA | 40 | 46 | 10 | H | 2 | Et | Et | OTHP |

TABLE 3-continued

| | | | | Intermediates of formulas II and III; Q = $(CH_2)_n$ | | | | |
|---|---|---|---|---|---|---|---|---|
| IIIB | 41 | 47 | 10 | H | 2 | Et | Et | OTHP |
| IIIA | 42 | 48 | 10 | H | 3 | Et | Et | OTHP |
| IIIB | 43 | 49 | 10 | H | 3 | Et | Et | OTHP |
| IIA | 44 | 50 | 8 | Me | 0 | Et | Et | $OSiMe_3$ |
| IIA | 45 | 51 | 8 | Et | 0 | Et | Et | $OSiMe_3$ |
| IIIA | 46 | 52 | 10 | Me | 0 | Et | Et | $OSiMe_3$ |
| IIIA | 47 | 53 | 10 | Et | 0 | Et | Et | $OSiMe_3$ |

TABLE 4

Exemplified Compounds of General Formula I, Q = $(CH_2)_n$

| Example Number | Compound Number | Isomer at C-22 | General Procedure | $R^3$ | n | $R^1$ | $R^2$ | X |
|---|---|---|---|---|---|---|---|---|
| 1 | 101 | A | 11 | H | 0 | Et | Et | OH |
| 2 | 102 | B | 11 | H | 0 | Et | Et | OH |
| 3 | 103 | A | 11 | Ac | 0 | Et | Et | OH |
| 4 | 104 | A | 11 | C(S)OPh | 0 | Et | Et | OH |
| 5 | 105 | A | 11 | H | 1 | Me | Me | OH |
| 6 | 106 | A | 11 | H | 1 | Et | Et | OH |
| 7 | 107 | B | 11 | H | 1 | Et | Et | OH |
| 8 | 108 | A | 12 | Me | 1 | Et | Et | OH |
| 9 | 109 | A | 12 | Et | 1 | Et | Et | OH |
| 10 | 110 | A | 12 | Bu | 1 | Et | Et | OH |
| 11 | 111 | A | 11 | i-Pen | 1 | Et | Et | OH |
| 12 | 112 | A | 11 | Bn | 1 | Et | Et | OH |
| 13 | 113 | A | 11 | Ac | 1 | Et | Et | OH |
| 14 | 114 | A | 11 | Piv | 1 | Et | Et | OH |
| 15 | 115 | A | 11 | H | 2 | Me | Me | OH |
| 16 | 116 | B | 11 | H | 2 | Me | Me | OH |
| 17 | 117 | A | 11 | H | 2 | Et | Et | OH |
| 18 | 118 | B | 11 | H | 2 | Et | Et | OH |
| 19 | 119 | A | 11 | H | 3 | Et | Et | OH |
| 20 | 120 | B | 11 | H | 3 | Et | Et | OH |
| | 121 | A | 11 or 12 | H | 0 | Me | Me | OH |
| | 122 | A | 11 or 12 | H | 0 | Me | Me | H |
| | 123 | A | 11 or 12 | H | 0 | Et | Et | H |
| | 124 | A | 11 or 12 | H | 0 | $CF_3$ | $CF_3$ | OH |
| | 125+ | A | 11 or 12 | H | 0 | Me | Et | OH |
| | 126++ | A | 11 or 12 | H | 0 | Me | Et | OH |
| | 127 | A | 11 or 12 | Me | 0 | Me | Me | OH |
| | 128 | A | 11 or 12 | Me | 0 | Me | Me | H |
| | 129 | A | 11 or 12 | Me | 0 | Et | Et | OH |
| 21 | 130 | A | 11 | Me | 0 | Et | Et | H |
| | 131 | A | 11 or 12 | Me | 0 | $CF_3$ | $CF_3$ | OH |
| | 132+ | A | 11 or 12 | Me | 0 | Me | Et | OH |
| | 133++ | A | 11 or 12 | Me | 0 | Me | Et | OH |
| | 134 | A | 11 or 12 | Et | 0 | Me | Me | OH |
| 22 | 135 | A | 11 | Et | 0 | Et | Et | OH |
| | 136 | A | 11 or 12 | H | 1 | Me | Me | H |
| | 137 | A | 11 or 12 | H | 1 | Et | Et | H |
| | 138 | A | 11 or 12 | H | 1 | $CF_3$ | $CF_3$ | OH |
| | 139+ | A | 11 or 12 | H | 1 | Me | Et | OH |
| | 140++ | A | 11 or 12 | H | 1 | Me | Et | OH |
| | 141 | A | 11 or 12 | Me | 1 | Me | Me | OH |
| | 142 | A | 11 or 12 | Me | 1 | Me | Me | H |
| | 143 | A | 11 or 12 | Me | 1 | Et | Et | H |
| | 144 | A | 11 or 12 | Me | 1 | $CF_3$ | $CF_3$ | OH |
| | 145+ | A | 11 or 12 | Me | 1 | Me | Et | OH |
| | 146++ | A | 11 or 12 | Me | 1 | Me | Et | OH |
| | 147 | A | 11 or 12 | Et | 1 | Me | Me | OH |
| | 148 | A | 11 or 12 | Me | 2 | Et | Et | OH |
| | 149 | A | 11 or 12 | Et | 2 | Et | Et | OH |

+(R) configuration at starred carbon atom
++(S) configuration at starred carbon atom The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral, administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and fluorinated $C_1$-$C_6$-alkyl hydrocarbons are especially preferred. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 μg, preferably from 0.2–25 μg, of a compound of formula I are administered. In the topical treatment of dermatological disorders, ointments, creams or lotions containing from 0.1–500 μg/g, and preferably from 0.1–100 μg/g, of a compound of formula I are administered. For topical use in ophthalmology ointments, drops or gels containing from 0.1–500 μg/g, and preferably from 0.1–100 μg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention will now be further described in the following non-limiting General Procedures, Preparations and Examples:

General Procedures- Preparations and Examples
General

The exemplified compounds I are listed in Table 4.

For nuclear magnetic resonance spectra (300 Mhz) chemical shift values (δ) are quoted for deuteriochloroform solutions relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

General Procedures

General Procedure 1

Protection of tertiary alcohols V or VII to give the corresponding trimethylsilyl compounds V or VI (Scheme 2. Table 1) (Preparation 1)

To a solution of the appropriate compound V or VII (0.043 mol) in dichloromethane (60 ml) was added N-ethyldiisopropylamine (6.1 g) and chlorotrimethylsilane (5.1 g) and the mixture was stirred at 20° C. for one hour. Phosphate buffer (pH 6.5, 0.07M, 60 ml) was added and after separation the organic phase was washed with saturated aqueous sodium chloride solution, dried and evaporated in vacuo to yield the title compound of the preparation.

General Procedure 2

Protection of tertiary alcohols V or VII to give the corresponding 2-tetrahydropyranyl compounds V or VI (Scheme 2. Table 1) (Preparations 2,4,6,8)

A mixture of the appropriate compound V or VII (0.01 mol), 3,4-dihydro-2M-pyran (1.26 g), PPTS (0.25 g) and dry dichloromethane (25 ml) was stirred under argon for 4 hours at 20° C. To the reaction mixture was added 100 ml of ether and 50 ml of semi-saturated aqueous sodium chloride solution. The organic phase was separated, dried and evaporated in vacuo to yield a crude product which was purified by chromatography (mixture of ether and pet.ether as eluant) to yield the title compound of the preparation.

General Procedure 3

Reaction of ketones $R^1R^2C=O$ with oraanometallic reagent prepared from propargylbromide and aluminium to give the corresponding tertiary alcohol V (Scheme 2. Table 2) (Preparation 3)

A mixture of aluminium scales (3.6 g), mercuric chloride (0.1 g) and dry THF (20 ml) was stirred at 20° C. for 20 minutes, under argon. A solution of propargyl bromide (23.8 g) in dry THF (20 ml) was added with stirring during 40 minutes, keeping the temperature at 25°–30° C. by intermittent cooling. The reaction mixture was stirred at 40°–45° C., heating as necessary, for 30 minutes. After cooling to about 25° C., a solution of the appropriate ketone, $R^1R^2C=O$ (0.2 mol) in dry ether (25 ml) was added during one hour, with stirring, cooling slightly to keep the temperature at about 25° C. Stirring was continued for a further half hour at 30°–35° C., after which the reaction mixture was worked up (ether). The residue was purified by distillation in vacuo through a 50 cm Podbielniak column to yield the title compound of the preparation as an oil.

General Procedure 4

Reaction of 4-pentinoic acid ethyl[1] ester with Grignard reagents, $R^1MgX^2$, to give the corresponding tertiary alcohol V (Scheme 2, Table 2) (Preparations 5 and 7) ($X^2$=Cl, Br, I)

[1] an equimolar amount of a different lower alkyl ester, e.g. the methyl or propyl ester may be used instead of the ethyl ester.

To 1.1 g magnesium turnings (Grignard quality) in a dry flask, was added dropwise with stirring a solution of the appropriate alkyl halide $R^1 X^2$ (0,045 mol) in dry ether (20 ml). The reaction took place under argon, with stirring, and with reflux, and lasted 20 minutes. Stirring and reflux was continued for a further 10 minutes.

This Grignard reagent was transferred to an addition funnel, under argon, and added dropwise with stirring and cooling to about −20° C., to a solution of 4-pentinoic acid ethyl1 ester (1.9 g) in dry ether (20 ml). The addition lasted 15 minutes, and after that stirring was continued for 20 minutes at −20° C. and for one hour at 30° C.

The reaction mixture was poured into a mixture of 100 g ice/water and 4N hydrochloric acid (15 ml) under stirring. After addition of aqueous sodium bicarbonate solution to render a pH of circa 5, the mixture was extracted twice with ether (25 ml each). The combined organic phases were washed with water and saturated aqueous sodium chloride solution, dried and evaporated in Vacuo to yield a crude product. This was purified either by distillation in vacuo or by chromatography (mixture of ether and pet. ether as eluant) to yield the title compound of the preparation.

General Procedures5

Conversion of TMS-protected alcohols of types V or VI to the corresponding THP-protected compound of type V or VI (Scheme 2. Table 2) (Preparation 9)

To a solution of the appropriate TMS-protected tertiary alcohol V or VI (0.02 mol) in methanol (25 ml) was added 5 drops of 6M hydrogen chloride in methanol and the mixture was stirred for 15 minutes at 20° C. The reaction mixture was evaporated until the methanol was removed, and the residue was redissolved in dichloromethane (40 ml). To this solution was added 3,4-dihydro-2-H-pyran (3.3 g) and PPTS (0.16 g) in portions under stirring and cooling in an ice-bath. After that, the mixture was stirred at 20° C. for three hours and then diluted with ether (200 ml). The ether phase was extracted with saturated aqueous sodium bicarbonate, water and saturated aqueous sodium chloride, dried and evaporated in vacuo to yield a crude product. This was purified by chromatography (mixture of ether and pet.ether as eluant) to yield the title compound of the preparation as an oil.

General Procedure 6

Conversion of compounds VI, with a terminal bromine atom, to the corresponding compound V, with a terminal ethinyl group (Scheme 2, Table 1) (Preparation 10)

Through dry liquid ammonia (circa 75 ml) dry acetylene was bubbled at a rate of about 200 ml per minute with stirring. At the same time sodium (0.5 g) was added in small pieces during 5 minutes. After about 5 minutes more, the flow of acetylene was discontinued, and the appropriate bromo-compound VI (3 mmol) was added during 5 minutes; stirring at room temperature was continued until all of the ammonia had evaporated (2 to 4 hours). Pet.ether (100 ml) and ice/water (100 g) was added under stirring. The organic phase was separated, washed several times with water until neutral, dried and evaporated in vacuo to yield a crude product. This was purified by chromatography (dichloromethane or mixture of dichloromethane and pet.ether as eluants) to yield the title compound of the preparation.

General Procedure 7

Reaction of Compound 1 with side chain building blocks V (RH) to yield Compounds IIA and IIB (Scheme 1. Table 3) (Preparations .11–13 and 21–23)

To a solution of the appropriate compound V (2.5 mmol) in dry THF (5 ml), cooled to $-70°$ C. and stirred under argon, was added dropwise, during 2 minutes, a solution of n-butyllithium (1.6 mM in hexane; 1.2 ml). Stirring was continued at $-70°$ C. for 10 minutes and then at 20° C. for one hour. The mixture was again cooled to $-70°$ C., and a solution of the aldehyde, compound 1 (0.57 g; 1 mmole) in dry THF (5 ml) was added dropwise, during 4 minutes, and after that, stirring was continued at $-70°$ C. for 15 minutes. The reaction mixture was worked up (ether) to yield a crude product containing compounds IIA and IIB which were separated and purified by chromatography (mixture of ether and pet.ether as eluant) to yield the title compounds of the preparation. (If necessary, repeated chromatography of selected fractions were performed, if convenient, in the form of PLC or on a Waters Prep-500 ®machine)General

General Procedure 8

Alkylation of C-22-hydroxy-compounds ($R^3=H$) of type II or III to the corresponding compound II or III where $R^3=C_1-C_{10}$ hydrocarbyl (Scheme 1. Table 3) (Preparations 14–18 and 44–45)

To a solution of the appropriate compound II or III ($R^3=H$) (0.5 mmol) in dry THF (5 ml) was added, while stirring at 20° C. under argon, a 20% suspension of potassium hydride in mineral oil (0.2 ml) followed by an alkylating agent, $R^3Z$ (1.5 mmol). Then, a solution of 18-Crown-6 (0.13 g) in dry THF (2 ml) was added, during 5 minutes. Stirring at 20° C. was continued for two hours, after which the reaction mixture was worked up (ether). The crude product was purified by chromatography (mixture of ether and pet.ether as eluant) to yield the title compound of the preparation.

General Procedure 9

Acylation of C-22-hydroxy-compounds ($R^3=H$) of type II or III to the corresponding compound II or III where $R^3=YR^4$ (Scheme 1, Table 3) (Preparations 19–20 and 26–27)

To a solution of the appropriate compound II or III ($R^3=H$) (0.25 mmol) in a suitable dry solvent, e.g. dichloromethane, was added, while stirring at 20° C. under argon, an acylating reagent ($R^4YCl$, $(R^4Y)_2O$ or $R^4YOH$), preferably accompanied by one or two suitable bases, such as triethylamine, pyridine and/or DMAP. In the case where an acid, $R^4YOH$, was used, the addition of a dehydrating or condensing agent such as e.g. dicyclohexyl carbodiimide was desirable. The reaction mixture was then stirred at a suitable temperature (from room temperature up to the boiling point of the solvent) for a sufficient time (typically for 1 to 4 hours). After a suitable work-up the crude product was purified by chromatography to yield the title compound of the preparation.

General Procedure 10

Isomerization of Compounds II or IV to the corresponding compound III or I (Scheme 1, Table 3) (Preparations 24–25, 28–43 and 46–47)

A solution of the appropriate compound II or IV (0.3 mmol), anthracene (70 mg) and triethylamine (0.05 ml) in dichloromethane (20 ml) under argon in a Pyrex flask was irradiated with UV-light from a high pressure ultraviolet lamp, type TQ760Z2 (Hanau) at about 10° C. for 20 minutes under stirring. The reaction mixture was concentrated in vacuo and treated with pet.ether ($2 \times 5$ ml). After filtering the filtrate was concentrated in vacuo and purified by chromatography (mixture of ether and pet.ether as eluant) to yield the title compound of the preparation or example.

General Procedure 11

Deprotection of Compounds II or III to the corresponding Compound IV or I by treatment with HF (Scheme 1. Table 4) (Examples 1–7 and 11–22)

To a solution of the appropriate compound II or III (0.07 mmol) in ethyl acetate (0.2 ml) was added acetonitrile (2 ml) followed by a 5% solution of hydrofluoric acid in acetonitrile:water, 7:1 (1.2 ml) under argon and with stirring. Stirring was continued for 45 minutes at 20° C. Saturated aqueous sodium bicarbonate solution (10 ml) was added, and the reaction mixture was worked up (ethyl acetate) The residue was purified by chromatography (ethyl acetate or a mixture of ethyl acetate and hexane or pentane as eluant) to yield the title compound of the preparation or example.

General Procedure 12

Deprotection of Compounds II or III to the corresponding Compounds IV or I by treatment with tetra-n-butylammoniumfluoride followed by pyridine-p-toluenesulfonate [2] (Scheme 1. Table 4) (Examples 8–10)

[2] or in the reverse order

To a solution of the appropriate compound II or III (0.16 mmol) in THF (5 ml) was added a solution of tetra-n-butylammonium fluoride (300 mg) in THF (5 ml) while stirring at 60° C. under argon. Stirring was continued for one hour at 60° C., and the reaction mixture was worked up (ethyl acetate with an additional extraction with aqueous sodium hydrogen carbonate). The residue after evaporation was purified by chromatography (50% to 0% pet.ether in ethyl acetate as eluant) and then dissolved in absolute ethyl alcohol (2 ml). PPTS (2 mg) was added, and the mixture was stirred for one hour at 50° C. under argon. After work-up (ethyl acetate with an additional aqueous sodium bicarbonate extraction) the residual crude product was purified by chromatography (50% to 0% pet.ether in ethyl acetate as eluant) to yield the title compound of the preparation or example.

Preparations

Preparation 1: Compound 2

Method: General Procedure 1.
Starting material V: 3-Ethyl-1-pentyn-3-ol.
NMR: $\delta=0.17$ (s, 9H), 0.95 (t, 6H), 1.63 (g, 4H), 2.42 (s, 1H).

Preparation 2: Compound 3

Method: General Procedure 2.
Starting material V: 1-Methyl-4-pentyn-2-ol.
Chromatography eluant: 5% ether in petroleum ether.
NMR: $\delta=1.34$ (s, 3H), 1.35 (s, 3H), 1.51 (m, 4H), 1.67 (m, 1H), 1.84 (m, 1H), 2.00 (t, 1H), 2.44 (m, 2H), 3.45 (m, 1H), 3.97 (m, 1H), 4.81 (m, 1H).

Preparation 3: Compound 4

Method: General Procedure 3.
Starting material: Diethyl ketone.
B.p. of Compound 4: 71°–72° C./30 mbar.
NMR: $\delta=0.90$ (t, 6H), 1.60 (m, 4H), 1.75 (s, 1H), 2.05 (t, 1H), 2.35 (m, 2H).

Preparation 4: Compound 5

Method: General Procedure 2.
Starting material V: Compound 4
Chromatography eluant: 0% to 5% ether in pet.ether.
NMR: $\delta=0.90$ (m, 6H), 1.45–1.92 (m, 10H), 1.96 (t, 1H), 2.46 (d, 2H), 3.47 (m, 1H), 3.98 (m, 1H), 4.81 (m, 1H).

Preparation 5: Compound 6

Method: General Procedure 4.
Starting material: Methyl magnesium iodide.
Purification by distillation in
B.p. of compound 4: 58°–59° C./12 mmHg.
NMR: $\delta=1.24$ (s, 6H), 1.69 (s, 1H), 1.75 (t, 2H), 1.98 (t, 1H), 2.31 (m, 2H).

Preparation 6: Compound 7

Method: General Procedure 2.
Starting material V: Compound 6
Chromatography eluant: 0% to 5% ether in pet. ether.
NMR: $\delta=1.21$ (s, 3H), 1.23 (s, 3H), 1.51 (m, 4H), 1.64 (m, 1H), 1.78 (t, 2H), 1.83 (m, 1H), 1.92 (t, 1H), 2.29 (m, 2H), 3.45 (m, 1H), 3.93 (m, 1H), 4.73 (m, 1H).

Preparation 7: Compound 8

Method: General Procedure 4.
Starting material: Ethyl magnesium bromide.
Chromatography eluant: 25% ether in pet. ether.
NMR: $\delta=0.87$ (t, 6H), 1.48 (m, 4H), 1.71 (m, 2H), 1.97 (t, 2H), 2.26 (m, 2H).

Preparation 8: Compound 9

Method: General Procedure 2.
Starting material V: Compound 8.
Chromatography eluant: 0% to 5% ether in pet. ether.
NMR: $\delta=0.84$ (m, 6H), 1.40–1.90 (m, 12H), 1.92 (t, 1H), 2.25 (m, 2H), 3.45 (m, 1H), 3.94 (m, 1H), 4.69 (m, 1H).

Preparation 9: Compound 10

Method: General Procedure 5.
Starting material VI: 1-Bromo-4-ethyl-4-trimethylsilyloxyhexane.
Chromatography eluant: 10% ether in pet.ether.
NMR: $\delta=0.83$ (m, 6H), 1.45–2.05 (m, 14H), 3.43 (t, 2H), 3.45 (m, 1H), 3.94 (m, 1H), 4.68 (m, 1H).

Preparation 10: Compound 11

Method: General Procedure 6.
Starting material VI: Compound 10.
Chromatography eluant: Dichloromethane.
NMR: $\delta=0.83$ (t, 6H), 1.54 (q, 4H), 1.45–1.90 (m, 10H), 1.95 (t, 1H), 2.17 (m, 2H), 3.44 (m, 1H), 3.95 (m, 1H), 4.69 (m, 1H).

Preparation 11: Compounds 12 and 13

Method: General Procedure 7.
Starting material V: Compound 2
Chromatography eluant: 10% to 20% ether in pet.ether.
NMR 12: $\delta=0.06$ (m, 12H), 0.16 (s, 9H), 0.55 (s, 3H), 0.86 (s, 9H), 0.89 (s, 9H), 0.94 (t, 6H), 1.04 (d, 3H), 1.30–2.00 (m, 18H), 2.06 (bt, 1H), 2.31 (bd, 1H), 2.55 (dd, 1H), 2.88 (dd, 1H), 4.21 (m, 1H), 4.52 (m, 1H), 4.66 (m, 1H), 4.94 (m, 1H), 4.98 (m, 1H), 5.83 (d, 1H), 6.45 (d, 1H).
NMR 13: $\delta=0.06$ (m, 12H), 0.18 (s, 9H), 0.56 (s, 3H), 0.86 (s, 9H), 0.89 (s, 9H), 0.96 (t, 6H), 1.00 (d, 3H), 1.20–2.10 (m, 19H), 2.30 (bd, 1H), 2.55 (dd, 1H), 2.87 (bd, 1H), 4.22 (m, 1H), 4.52 (m, 1H), 4.67 (m, 1H), 4.94 (m, 1H), 4.98 (m, 1H), 5.82 (d, 1H), 6.44 (d, 1H).

Preparation 12: Compound 14

Method: General Procedure 7.
Starting material V: Compound 3.
Chromatography eluant: 20% to 25% ether in pet.ether.
NMR: $\delta=0.05$ (m, 12H), 0.54 (s, 3H), 0.85 (s, 9H), 0.89 (s, 9H), 1.03 (d, 3H), 1.31 (s, 3H), 1.32 (s, 3H), 1.25–1.97 (m, 20H), 2.05 (bt, 1H), 2.33 (bd, 1H), 2.45 (m, 2H), 2.54 (dd, 1H), 2.87 (dd, 1H), 3.44 (m, 1H), 3.94 (m, 1H), 4.21 (m, 1H), 4.52 (m, 1H), 4.60 (m, 1H), 4.79 (m, 1H), 4.93 (m, 1H), 4.98 (m, 1H), 5.82 (d, 1H), 6.44 (d, 1H).

Preparation 13: Compounds 15 and 16

Method: General Procedure 7.
Starting material V: Compound 5.
Chromatography eluant: 20% to 33% ether in pet.ether.
NMR 15: $\delta=0.05$ (m, 12H), 0.54 (s, 3H), 0.85 (s, 9H), 0.86 (m, 6H), 0.89 (s, 9H), 1.02 (d, 3H), 1.25–1.97 (m, 24H), 2.04 (bt, 1H), 2.30 (bd, 1H), 2.46 (m, 2H), 2.54 (dd, 1H), 2.87 (dd, 1H), 3.45 (m, 1H), 3.96 (m, 1H), 4.21 (m, 1H), 4.52 (m, 1H), 4.57 (m, 1H), 4.80 (m, 1H), 4.93 (m, 1H), 4.97 (m, 1H), 5.82 (d, 1H), 6.44 (d, 1H).
NMR 16: $\delta=0.05$ (m, 12H), 0.55 (s, 3H), 0.85 (s, 9H), 0.88 (m, 6H), 0.89 (s, 9H), 0.98 (d, 3H), 1.30–1.97 (m, 24H), 2.02 (bt, 1H), 2.30 (bd, 1H), 2.49 (m, 2H), 2.54 (dd, 1H), 2.87 (dd, 1H), 3.45 (m, 1H), 3.95 (m, 1H), 4.21 (m, 1H), 4.52 (m, 1H), 4.61 (m, 1H), 4.80 (m, 1H), 4.93 (m, 1H), 4.97 (m, 1H), 5.82 (d, 1H), 6.44 (d, 1H).

Preparation 14: Compound 17

Method: General Procedure 8.
Starting material I IA: Compound 15.

Alkylating agent: R³Z: Methyl iodide.
Chromatography eluant: 0% to 10% ether in pet.ether.

NMR: δ=0.05 (m, 12H), 0.53 (s, 3H), 0.85 (s, 9H), 0.89 (s, 9H), 0.90 (m, 6H), 1.01 (d, 3H), 1.25-1.98 (m, 23H), 2.04 (bt, 1H), 2.31 (bd, 1H), 2.48 (m, 2H), 2.55 (dd, 1H), 2.87 (m, 1H), 3.33 (s, 3H), 3.45 (m, 1H), 3.96 (m, 1H), 4.09 (m, 1H), 4.21 (m, 1H), 4.52 (m, 1H), 4.80 (m, 1H), 4.93 (m, 1H), 4.97 (m, 1H), 5.81 (d, 1H), 6.44 (d, 1H).

Preparation 15: Compound 18

Method: General Procedure 8.
Starting material I IA: Compound 15.
Alkylating agent: R³Z: Ethyl bromide.
Chromatography eluant: 0% to 10% ether in pet.ether.

NMR: δ=0.05 (m, 12H), 0.53 (s, 3H), 0.85 (s, 9H), 0.87 (t, 6H), 0.89 (s, 9H), 1.01 (d, 3H), 1.17 (t, 3H), 1.25-1.98 (m, 23H), 2.04 (bt, 1H), 2.30 (bd, 1H), 2.47 (m, 2H), 2.55 (dd, 1H), 2.87 (dd, 1H), 3.28 (m, 1H), 3.45 (m, 1H), 3.74 (m, 1H), 3.96 (m, 1H), 4.15 (m, 1H), 4.21 (m, 1H), 4.52 (m, 1H), 4.80 (m, 1H), 4.93 (m, 1H), 4.97 (m, 1H), 5.81 (d, 1H), 6.44 (d, 1H).

Preparation 16: Compound 19

Method: General Procedure 8.
Starting material I IA: Compound 15.
Alkylating agent: R³Z: n-Butyl bromide.
Chromatography eluant: 0% to 10% ether in pet.ether.

NMR: δ=0.05 (m, 12H), 0.52 (s, 3H), 0.85 (s, 9H), 0.90 (s, 9H), 0.85-0.95 (m, 9H), 1.01 (d, 3H), 1.20-1.98 (m, 27H), 2.03 (bt, 1H), 2.30 (bd, 1H), 2.47 (m, 2H), 2.55 (dd, 1H), 2.87 (m, 1H), 3.21 (m, 1H), 3.44 (m, 1H), 3.68 (m, 1H), 3.96 (m, 1H), 4.12 (m, 1H), 4.21 (m, 1H), 4.53 (m, 1H), 4.80 (m, 1H), 4.93 (m, 1H), 4.98 (m, 1H), 5.81 (d, 1H), 6.45 (d, 1H).

Preparation 17: Compound 20

Method: General Procedure 8.
Starting material I IA: Compound 15
Alkylating agent: R³Z: 1-Bromo-3-methylbutane.
Chromatography eluant: 0% to 10% ether in pet.ether.

NMR: δ=0.05 (m, 12H), 0.52 (s, 3H), 0.86 (s, 9H), 0.88 (t, 6H), 0.90 (s, 9H), 0.90 (d, 6H), 1.00 (d, 3H), 1.15-1.97 (m, 26H), 2.03 (bt, 1H), 2.30 (bd, 1H), 2.47 (m, 2H), 2.55 (dd, 1H), 2.87 (dd, 1H), 3.23 (m, 1H), 3.44 (m, 1H), 3.72 (m, 1H), 3.97 (m, 1H), 4.11 (m, 1H), 4.21 (m, 1H), 4.52 (m, 1H), 4.80 (m, 1H), 4.93 (m, 1H), 4.98 (m, 1H), 5.81 (d, 1H), 6.45 (d, 1H).

Preparation 18: Compound 21

Method: General Procedure 8.
Starting material IIA: Compound 15.
Alkylating agent: R³Z: Benzyl bromide.
Chromatography eluant: 0% to 108 ether in pet.ether.
NMR: δ=0.06 (m, 12H), 0.53 (s, 3H), 0.86 (s, 9H), 0.90 (s, 9H), 0.91 (t, 6H), 1.07 (d, 3H), 1.15-1.97 (m, 23H), 2.02 (bt, 1H), 2.30 (bd, 1H), 2.51 (m, 2H), 2.55 (dd, 1H), 2.84 (bd, 1H), 3.45 (m, 1H), 3.97 (m, 1H), 4.21 (m, 1H), 4.28 (m, 1H), 4.38 (d, 1H), 4.53 (m, 1H), 4.78 (d, 1H), 4.82 (m, 1H), 4.93 (m, 1H), 4.98 (m, 1H), 5.81 (d, 1H), 6.44 (d, 1H), 7.23-7.40 (m, 5H).

Preparation 19: Compound 22

Method: General Procedure 9.
Starting material IIA: Compound 15.
Acylating reagent: Acetic anhydride (0.2 ml).
Base: DMAP (30 mg).
Solvent: Dichloromethane (20 ml).
Reaction temperature: 40° C.
Reaction time: 3 hours.
Work up: Concentration in vacuo.
Chromatography eluant: 0% to 20% ether in pet.ether.

NMR: δ=0.05 (m, 12H), 0.52 (s, 3H), 0.85 (s, 9H), 0.87 (m, 6H), 0.89 (s, 9H), 1.07 (d, 3H), 2.05 (s, 3H), 1.10-2.10 (m, 24H), 2.29 (bd, 1H), 2.45 (m, 2H), 2.54 (dd, 1H), 2.86 (dd, 1H), 3.43 (m, 1H), 3.94 (m, 1H), 4.21 (m, 1H), 4.52 (m, 1H), 4.77 (m, 1H), 4.93 (m, 1H), 4.97 (m, 1H), 5.35 (m, 1H), 5.81 (d, 1H), 6.43 (d, 1H).

Preparation 20: Compound 23

Method: General Procedure 9.
Starting material IIA: Compound 15.
Acylating reagent: Pivaloyl chloride (150 mg).
Bases: Triethylamine (200 mg), DMAP (30 mg).
Solvent: Dichloromethane (10 ml).
Reaction temperature: 40° C.
Reaction time: 1.5 hours.
Work up: Ether.
Chromatography eluant: 0% to 20% ether in pet.ether.

NMR: δ=0.05 (m, 12H), 0.54 (s, 3H), 0.85 (s, 9H), 0.87 (t, 6H), 0.89 (s, 9H)., 1.10 (d, 3H), 1.20 (s, 9H), 1.05-2.07 (m, 24H), 2.29 (bd, 1H), 2.44 (bs, 2H), 2.55 (dd, 1H), 2.86 (dd, 1H), 3.44 (m, 1H), 3.94 (m, 1H), 4.21 (m, 1H), 4.52 (m, 1H), 4.77 (m, 1H), 4.93 (m, 1H), 4.97 (m, 1H), 5.31 (m, 1H), 5.81 (d, 1H), 6.43 (d, 1H).

Preparation 21: Compounds 24 and 25

Method: General Procedure 7.
Starting material V: Compound 7.
Chromatography eluant: 15% to 33% ether in pet.ether.

NMR 24:δ=0.05 (m, 12H), 0.54 (s, 3H), 0.85 (s, 9H), 0.89 (s, 9H), 1.02 (d, 3H), 1.19 (s, 3H), 1.21 (s, 3H), 1.30-1.98 (m, 22H), 2.04 (bt, 1H), 2.17-2.40 (m, 3H), 2.54 (dd, 1H), 2.87 (dd, 1H), 3.43 (m, 1H), 3.93 (m, 1H), 4.21 (m, 1H), 4.53 (m, 1H), 4.57 (m, 1H), 4.70 (m, 1H), 4.93 (m, 1H), 4.97 (m, 1H), 5.82 (d, 1H), 6.44 (d, 1H).

NMR 25:δ=0.05 (m, 12H), 0.54 (s, 3H), 0.85 (s, 9H), 0.89 (s, 9H), 0.97 (d, 3H), 1.20 (s, 3H), 1.23 (s, 3H), 1.17-1.98 (m, 22H), 2.04 (bt, 1H), 2.20-2.44 (m, 3H), 2.55 (dd, 1H), 2.87 (dd, 1H), 3.44 (m, 1H), 3.92 (m, 1H), 4.21 (m, 1H), 4.52 (m, 1H), 4.57 (m, 1H), 4.71 (m, 1H), 4.93 (m, 1H), 4.97 (m, 1H), 5.82 (d, 1H), 6.44 (d, 1H).

Preparation 22: Compounds 26 and 27

Method: General Procedure 7.
Starting material V: Compound 9.
Chromatography eluant: 15% to 33% ether in pet.ether.

NMR 26:δ=0.05 (m, 12H), 0.55 (s, 3H), 0.82 (t, 6H), 0.85 (s, 9H), 0.89 (s, 9H), 1.02 (d, 3H), 1.25-1.98 (m, 26H), 2.05 (bt, 1H), 2.12-2.38 (m, 3H), 2.54 (dd, 1H), 2.87 (dd, 1H), 3.44 (m, 1H), 3.93 (m, 1H), 4.21 (m, 1H), 4.52 (m, 1H), 4.57 (m, 1H), 4.68 (m, 1H), 4.93 (m, 1H), 4.98 (m, 1H), 5.82 (d, 1H), 6.44 (d, 1H).

NMR 27:δ=0.04 (m, 12H), 0.54 (s, 3H), 0.82 (t, 6H), 0.85 (s, 9H), 0.88 (s, 9H), 0.97 (d, 3H), 1.10-1.97 (m, 26H), 2.03 (bt, 1H), 2.12-2.42 (m, 3H), 2.54 (dd, 1H), 2.86 (dd, 1H), 3.44 (m, 1H), 3.93 (m, 1H), 4.21 (m, 1H), 4.52 (m, 1H), 4.56 (m, 1H), 4.67 (m, 1H), 4.93 (m, 1H), 4.97 (m, 1H), 5.82 (d, 1H), 6.44 (d, 1H).

Preparation 23: Compounds 28 and 29

Method: General Procedure 7.
Starting material V: Compound 11.
Chromatography eluant: 15% to 20% ether in pet.ether.
NMR 28:$\delta$=0.05 (m, 12H), 0.54 (s, 3H), 0.81 (t, 6H), 0.85 (s, 9H), 0.89 (d, 9H), 1.02 (d, 3H), 1.27–1.98 (m, 28H), 2.05 (bt, 1H), 2.17 (m, 2H), 2.30 (bd, 1H), 2.54 (dd, 1H), 2.87 (dd, 1H), 3.44 (m, 1H), 3.94 (m, 1H), 4.21 (m, 1H), 4.52 (m, 1H), 4.57 (m, 1H), 4.70 (m, 1H), 4.93 (m, 1H), 4.97 (m, 1H), 5.82 (d, 1H), 6.44 (d, 1H).
NMR 29:$\delta$=0.05 (m, 12H), 0.55 (s, 3H), 0.82 (t, 6H), 0.85 (s, 9H), 0.89 (d, 9H), 0.98 (4, 3H), 1.25–2.10 (m, 29H), 2.22 (m, 2H), 2.29 (bd, 1H), 2.55 (dd, 1H), 2.87 (dd, 1H), 3.44 (m, 1H), 3.94 (m, 1H), 4.21 (m, 1H), 4.52 (m, 1H), 4.59 (m, 1H), 4.71 (m, 1H), 4.93 (m, 1H), 4.97 (m, 1H), 5.82 (d, 1H), 6.44 (d, 1H).

Preparation 24: Compound 30

Method: General Procedure 10.
Starting material I IA: Compound 12.
Chromatography eluant: 10% ether in pet.ether.
NMR: $\delta$=0.05 (m, 12H), 0.16 (s, 9H), 0.54 (s, 3H), 0.86 (s, 9H), 0.87 (s, 9H), 0.94 (m, 6H), 1.03 (d, 3H), 1.20–1.95 (m 18H), 2.01 (bt, 1H), 2.21 (dd, 1H), 2.44 (dd, 1H), 2.82 (m, 1H), 4.18 (m, 1H), 4.36 (m, 1H), 4.66 (m, 1H), 4.85 (m, 1H), 5.17 (m, 1H), 6.01 (d, 1H), 6.22 (d, 1H).

Preparation 25: Compound 31

Method: Genera 1 Procedure 10.
Starting material IIB: Compound 13.
Chromatography eluant: 0% to 12% ether in pet.ether.
NMR: $\delta$=0.05 (m, 12H), 0.18 (s, 9H), 0.55 (s, 3H), 0.87 (s, 18H), 0.96 (m, 6H), 0.99 (d, 3H), 1.10–2.10 (m, 19H), 2.20 (dd, 1H), 2.44 (dd, 1H), 2.82 (m, 1H), 4.18 (m, 1H), 4.35 (m, 1H), 4.67 (d, 1H), 4.85 (d, 1H), 5.17 (d, 1H), 6.01 (d, 1H), 6.22 (d, 1H).

Preparation 26: Compound 32

Method: General Procedure 9.
Starting material IIIA: Compound 30.
Acylating reagent: Acetic acid (0.02 ml).
Dehydrating agent: Dicyclohexyl carbodiimide (66 mg).
Base: DMAP (7 mg).
Solvent: Dichloromethane (3 ml).
Reaction temperature: 20 ° C.
Reaction time: 4 hours.
Work up: Filtration, concentration of the filtrate in vacuo.

Chromatography eluant: 10% ether in pet.ether.

NMR: $\delta$=0.05 (m, 12H), 0.14 (s, 9H), 0.52 (s, 3H), 0.86 (s, 18H), 0.92 (t, 6H), 1.08 (d, 3H), 1.05–2.05 (m, 18H), 2.05 (s, 3H), 2.20 (dd, 1H), 2.43 (dd, 1H), 2.82 (m, 1H), 4.18 (m, 1H), 4.36 (m, 1H), 4.85 (m, 1H), 5.17 (m, 1H), 5.42 (d, 1H), 6.00 (d, 1H), 6.21 (d, 1H).

Preparation 27: Compound 33

Method: General Procedure 9.
Starting material IIIA: Compound 30.
Acylating reagent: Phenyl chlorothionoformate (125 mg).
Base: Pyridine (0.2 ml).
Solvent: Dichloromethane (5 ml).
Reaction temperature: 20° C.
Reaction time: 3 hours.
Work up: Dichloromethane.
Chromatography eluant: 4% ether in pet.ether.
NMR: $\delta$=0.06 (m, 12H), 0.18 (s, 9H), 0.56 (s, 3H), 0.87 (s, 9H), 0.88 (s, 9H), 0.96 (t, 6H), 1.16 (d, 3H), 1.10–2.10 (m, 18H), 2.21 (dd, 1H), 2.44 (dd, 1H), 2.84 (m, 1H), 4.19 (m, 1H), 4.37 (m, 1H), 4.86 (m, 1H), 5.18 (m, 1H), 5.78 (d, 1H), 6.02 (d, 1H), 6.23 (d, 1H), 7.08 (m, 2H), 7.28 (m, 1H), 7.42 (m, 2H).

Preparation 28: Compound 34

Method: General Procedure 10.
Starting material I IA: Compound 14.
Chromatography eluant: 20% to 25% ether in pet.ether.
NMR: $\delta$=0.05 (m, 12H), 0.53 (s, 3H), 0.87 (s, 18H), 1.02 (d, 3H), 1.31 (s, 3H), 1.32 (s, 3H), 1.15–1.94 (m, 2OH), 2.00 (bt, 1H), 2.20 (dd, 1H), 2.44 (dd, 1H), 2.45 (m, 2H), 2.82 (dd, 1H), 3.44 (m, 1H), 3.95 (m, 1H), 4.18 (m, 1H), 4.36 (m, 1H), 4.60 (m, 1H), 4.80 (m, 1H), 4.85 (m, 1H), 5.17 (m, 1H), 6.01 (d, 1H), 6.22 (d, 1H).

Preparation 29: Compound 35

Method: General Procedure 10.
Starting material IIA: Compound 15.
Chromatography eluant: 20% to 25% ether in pet.ether.
NMR: $\delta$=0.05 (m, 12H), 0.53 (s, 3H), 0.87 (s, 18H), 0.90 (m, 6H), 1.01 (d, 3H), 1.15–1.94 (m, 24H), 1.99 (bt, 1H), 2.20 (dd, 1H), 2.44 (dd, 1H), 2.46 (m, 2H), 2.81 (dd, 1H), 3.43 (m, 1H), 3.95 (m, 1H), 4.17 (m, 1H), 4.36 (m, 1H), 4.57 (m, 1H), 4.80 (m, 1H), 4.85 (m, 1H), 5.17 (m, 1H), 6.01 (d, 1H), 6.22 (d, 1H).

Preparation 30: Compound 36

Method: General Procedure 10.
Starting material IIB: Compound 16.
Chromatography eluant: 15% to 25% ether in pet.ether.
NMR: $\delta$=0.05 (m, 12H), 0.54 (s, 3H), 0.87 (s, 18H), 0.89 (m, 6H), 0.97 (d, 3H), 1.15–1.92 (m, 24H), 1.97 (bt, 1H), 2.20 (dd, 1H), 2.44 (dd, 1H), 2.49 (m, 2H), 2.81 (dd, 1H), 3.45 (m, 1H), 3.96 (m, 1H), 4.17 (m, 1H), 4.36 (m, 1H), 4.61 (m, 1H), 4.81 (m, 1H), 4.85 (m, 1H), 5.17 (m, 1H), 6.01 (d, 1H), 6.22 (d, 1H).

Preparation 31: Compound 37

Method: General Procedure 10.
Starting material IIA: Compound 17.
Chromatography eluant: 5% to 10% ether in pet.ether.
NMR: $\delta$=0.05 (m, 12H), 0.52 (s, 3H), 0.87 (s, 18H), 0.89 (m, 6H), 1.00 (d, 3H), 1.20–1.93 (m, 23H), 1.99 (bt, 1H), 2.20 (dd, 1H), 2.44 (dd, 1H), 2.48 (m, 2H), 2.82 (m, 1H), 3.33 (s, 3H), 3.44 (m, 1H), 3.96 (m, 1H), 4.10 (m, 1H), 4.18 (m, 1H), 4.36 (m, 1H), 4.80 (m, 1H), 4.85 (m, 1H), 5.17 (m, 1H), 6.01 (d, 1H), 6.22 (d, 1H).

Preparation 32: Compound 38

Method: General Procedure 10.
Starting material IIA: Compound 18.
Chromatography eluant: 0% to 10% ether in pet.ether.
NMR: $\delta$=0.05 (m, 12H), 0.51 (s, 3H), 0.86 (s, 18H), 0.88 (m, 6H), 1.00 (d, 3H), 1.18 (t, 3H), 1.25–1.92 (m, 23H), 1.99 (bt, 1H), 2.20 (dd, 1H), 2.43 (dd, 1H), 2.46 (m, 2H), 2.82 (dd, 1H), 3.28 (m, 1H), 3.44 (m, 1H), 3.75 (m, 1H), 3.97 (m, 1H), 4.15 (m, 1H), 4.18 (m, 1H), 4.36 (m, 1H), 4.80 (m, 1H), 4.86 (m, 1H), 5.17 (m, 1H), 6.01 (d, 1H), 6.22 (d, 1H).

Preparation 33: Compound 39

Method: General Procedure 10.
Starting material IIA: Compound 19.
Chromatography eluant: 5% to 10% ether in pet.ether.
NMR: δ–0.05 (m, 12H), 0.51 (s, 3H), 0.87 (s, 18H), 0.85–0.95 (m, 9H), 1.00 (d, 3H), 1.20–1.93 (m, 27H), 1.98 (bt, 1H), 2.20 (dd, 1H), 2.44 (dd, 1H), 2.47 (m, 2H), 2.82 (m, 1H), 3.21 (m, 1H), 3.44 (m, 1H), 3.68 (m, 1H), 3.96 (m, 1H), 4.12 (m, 1H), 4.18 (m, 1H), 4.36 (m, 1H), 4.81 (m, 1H), 4.85 (m, 1H), 5.17 (m, 1H), 6.01 (d, 1H), 6.23 (d, 1H).

Preparation 34: Compound 40

Method: General Procedure 10.
Starting material IIA: Compound 20.
Chromatography eluant: 0% to 5% ether in pet.ether.
NMR: δ=0.05 (m, 12H), 0.51 (s, 3H), 0.86 (s, 18H), 0.88 (m, 12H), 0.99 (d, 3H), 1.15–1.92 (m, 26H), 1.98 (bt, 1H), 2.20 (dd, 1H), 2.43 (dd, 1H), 2.47 (m, 2H), 2.82 (bd, 1H), 3.22 (m, 1H), 3.44 (m, 1H), 3.71 (m, 1H), 3.96 (m, 1H), 4.11 (m, 1H), 4.17 (m, 1H), 4.36 (m, 1H), 4.80 (m, 1H), 4.85 (m, 1H), 5.17 (m, 1H), 6.00 (d, 1H), 6.22 (d, 1H).

Preparation 35: Compound 41

Method: General Procedure 10.
Starting material IIA: Compound 21.
Chromatography eluant: 0% to 10% ether in pet.ether.
NMR: δ=0.05 (m, 12H), 0.51 (s, 3H), 0.86 (s, 18H), 0.90 (m, 6H), 1.05 (d, 3H), 1.15–1.90 (m, 23H), 1.97 (bt, 1H), 2.20 (dd, 1H), 2.43 (dd, 1H), 2.51 (m, 2H), 2.79 (bd, 1H), 3.45 (m, 1H), 3.96 (m, 1H), 4.18 (m, 1H), 4.27 (m, 1H), 4.36 (m, 1H), 4.38 (d, 1H), 4.77 (d, 1H), 4.82 (m, 1H), 4.85 (m, 1H), 5.17 (m, 1H), 6.00 (d, 1H), 6.22 (d, 1H), 7.34 (m, 5H).

Preparation 36: Compound 42

Method: General Procedure 10.
Starting material I IA: Compound 22.
Chromatography eluant: 0% to 20% ether in pet.ether.
NMR: δ=0.05 (m, 12H), 0.51 (s, 3H), 0.86 (s, 18H), 0.83–0.92 (m, 6H), 1.07 (d, 3H), 1.00–1.91 (m, 23H), 1.96 (bt, 1H), 2.05 (s, 3H), 2.20 (dd, 1H), 2.43 (dd, 1H), 2.46 (m, 2H), 2.81 (dd, 1H), 3.43 (m, 1H), 3.94 (m, 1H), 4.17 (m, 1H), 4.36 (m, 1H), 4.78 (m, 1H), 4.84 (m, 1H), 5.16 (m, 1H), 5.34 (m, 1H), 6.00 (d, 1H), 6.21 (d, 1H).

Preparation 37: Compound 43

Method: General Procedure 10.
Starting material IIA: Compound 23.
Chromatography eluant: 0% to 20% ether in pet.ether.
NMR: δ=0.05 (m, 12H), 0.52 (s, 3H), 0.86 (s, 18H), 0.82–0.90 (m, 6H), 1.09 (d, 3H), 1.20 (s, 9H), 1.00–1.90 (m, 23H), 1.94 (bt, 1H), 2.18 (dd, 1H), 2.43 (dd, 1H), 2.44 (bs, 2H), 2.81 (dd, 1H), 3.43 (m, 1H), 3.94 (m, 1H), 4.17 (m, 1H), 4.35 (m, 1H), 4.76 (m, 1H), 4.84 (m, 1H), 5.16 (m, 1H), 5.31 (m, 1H), 6.00 (d, 1H), 6.21 (d, 1H).

Preparation 38: Compound 44

Method: General Procedure 10.
Starting material IIA: Compound 24.
Chromatography eluant: 15% to 25% ether in pet.ether.
NMR: δ=0.05 (m, 12H), 0.53 (s, 3H), 0.86 (s, 18H), 1.01 (d, 3H), 1.18 (s, 3H), 1.21 (s, 3H), 1.73 (t, 2H), 1.15–1.98 (m, 20H), 1.99 (bt, 1H), 2.20 (dd, 1H), 2.29 (m, 2H), 2.43 (dd, 1H), 2.82 (dd, 1H), 3.45 (m, 1H), 3.92 (m, 1H), 4.17 (m, 1H), 4.36 (m, 1H), 4.57 (m, 1H), 4.70 (m, 1H), 4.85 (m, 1H), 5.17 (m, 1H), 6.01 (d, 1H), 6.22 (d, 1H).

Preparation 39: Compound 45

Method: General Procedure 10.
Starting material IIB: Compound 25.
Chromatography eluant: 20% to 25% ether in pet.ether.
NMR: δ=0.05 (m, 12H), 0.53 (s, 3H), 0.86 (s, 18H), 0.96 (d, 3H), 1.20 (s, 3H), 1.23 (s, 3H), 1.75 (t, 2H), 1.12–1.92 (m, 20H), 1.99 (bt, 1H), 2.20 (dd, 1H), 2.31 (m, 2H), 2.43 (dd, 1H), 2.82 (dd, 1H), 3.44 (m, 1H), 3.92 (m, 1H), 4.19 (m, 1H), 4.36 (m, 1H), 4.57 (m, 1H), 4.70 (m, 1H), 4.85 (m, 1H), 5.17 (m, 1H), 6.01 (d, 1H), 6.22 (d, 1H).

Preparation 40: Compound 46

Method: General Procedure 10.
Starting material I IA: Compound 26.
Chromatography eluant: 20% to 25% ether in pet.ether.
NMR: δ– 0.05 (m, 12H), 0.53 (s, 3H), 0.82 (m, 6H), 0.86 (s, 18H), 1.01 (d, 3H), 1.72 (t, 2H), 1.25–1.93 (m, 24H), 2.00 (bt, 1H), 2.20 (dd, 1H), 2.23 (m, 2H), 2.43 (d, 1H), 2.82 (dd, 1H), 3.44 (m, 1H), 3.93 (m, 1H), 4.18 (m, 1H), 4.36 (m, 1H), 4.57 (.m, 1H), 4.67 (m, 1H), 4.85 (m, 1H), 5.17 (m, 1H), 6.01 (d, 1H), 6.22 (d, 1H).

Preparation 41: Compound 47

Method: General Procedure 10.
Starting material IIB: Compound 27.
Chromatography eluant: 20% to 25% ether in pet.ether.
NMR: δ=0.05 (m, 12H), 0.53 (s, 3H), 0.83 (t, 6H), 0.86 (s, 18H), 0.96 (d, 3H), 1.12–1.93 (m, 26H), 1.98 (bt, 1H), 2.10–2.40 (m, 3H), 2.43 (dd, 1H), 2.81 (dd, 1H), 3.44 (m, 1H), 3.93 (m, 1H), 4.18 (m, 1H), 4.35 (m, 1H), 4.57 (m, 1H), 4.67 (m, 1H), 4.85 (m, 1H), 5.17 (m, 1H), 6.01 (d, 1H), 6.22 (d, 1H).

Preparation 42: Compound 48

Method: General Procedure 10.
Starting material IIA: Compound 28.
Chromatography eluant: 0% to 20% ether in pet.ether.
NMR: δ=0.05 (m, 12H), 0.53 (s, 3H), 0.81 (t, 6H), 0.86 (s, 18H), 1.02 (d, 3H), 1.25–1.93 (m, 28H), 2.00 (bt, 1H), 2.18 (m, 2H), 2.20 (dd, 1H), 2.43 (dd, 1H), 2.82 (dd, 1H), 3.43 (m, 1H), 3.94 (m, 1H), 4.18 (m, 1H), 4.36 (m, 1H), 4.57 (m, 1H), 4.70 (m, 1H), 4.85 (m, 1H), 5.17 (m, 1H), 6.01 (d, 1H), 6.22 (d, 1H).

Preparation 43: Compound 49

Method: General Procedure 10.
Starting material IIB: Compound 29.
Chromatography eluant: 0% to 20% ether in pet.ether.

NMR: δ=0.05 (m, 12H), 0.54 (s, 3H), 0.82 (t, 6H), 0.86 (s, 18H), 0.97 (d, 3H), 1.15–2.05 (m, 29H), 2.20 (dd, 1H), 2.21 (m, 1H), 2.43 (dd, 1H), 2.82 (dd, 1H), 3.44 (m, 1H), 3.94 (m, 1H), 4.18 (m, 1H), 4.35 (m, 1H), 4.59 (m, 1H), 4.71 (m, 1H), 4,85 (m, 1H), 5.17 (m, 1H), 6.01 (d, 1H), 6.22 (d, 1H).

Preparation 44: Compound 50

Method: General Procedure 8.
Starting material IIA: Compound 12.
Alkylating agent: R³Z: Methyl iodide.
Chromatography eluant: 0% to 10% ether in pet.ether.
NMR: δ=0.06 (m, 12H), 0.17 (s, 9H), 0.54 (s, 3H), 0.86 (s, 9H ), 0.89 (s, 9H ), 0.96 (dt, 6H ), 1.03 (d, 3H ), 1.64 (q, 4H), 1.15–2.12 (m, 14H), 2.31 (bd, 1H), 2.55 (dd, 1H), 2.87 (m, 1H), 3.36 (s, 3H), 4.17 (d, 1H), 4.21 (m, 1H), 4.53 (m, 1H), 4.93 (m, 1H), 4.98 (m, 1H), 5.82 (d, 1H), 6.45 (d, 1H).

Preparation 45: Compound 51

Method: General Procedure 8.
Starting material IIA: Compound
Alkylating agent: R³Z: Ethyl bromide.
Chromatography eluant: 0% to 10% ether in pet.ether.
NMR: δ=0.06 (m, 12H), 0.16 (s, 9H), 0.53 (s, 3H), 0.85 (s, 9H), 0.89 (s, 9H), 0.95 (t, 6H), 1.03 (d, 3H), 1.18 (t, 3H), 1.63 (q, 4H), 1.10–2.15 (m, 14H), 2.31 (bd, 1H), 2.55 (dd, 1H), 2.88 (m, 1H), 3.30 (m, 1H), 3.77 (m, 1H), 4.21 (d, 1H), 4.21 (m, 1H), 4.53 (m, 1H), 4.93 (m, 1H), 4.98 (m, 1H), 5.82 (d, 1H), 6.45 (d, 1H).

Preparation 46: Compound 52

Method: General Procedure 10.
Starting material I IA: Compound 50.
Chromatography eluant: 0% to 20% ether in pet.ether.
NMR: δ=0.06 (m, 12H), 0.17 (s, 9H), 0.53 (s, 3H), 0.87 (s, 18H), 0.96 (dt, 6H), 1.02 (d, 3H), 1.63 (q, 4H), 1.15–2.10 (m, 14H), 2.21 (dd, 1H), 2.45 (dd, 1H), 2.82 (m, 1H), 3.36 (s, 3H), 4.16 (d, 1H), 4.19 (m, 1H), 4.38 (m, 1H), 4.86 (m, 1H), 5.18 (m, 1H), 6.01 (d, 1H), 6.23 (d, 1H).

Preparation 47: Compound 53

Method: General Procedure 10.
Starting material IIA: Compound 51.
Chromatography eluant: 0% to 10% ether in pet.ether.
NMR: δ=0.05 (m, 12H), 0.16 (s, 9H), 0.52 (s, 3H), 0.87 (s, 18H), 0.95 (t, 6H), 1.02 (d, 3H), 1.18 (t, 3H), 1.63 (q, 4H), 1.12–2.10 (m, 14H), 2.21 (dd, 1H), 2.44 (dd, 1H), 2.82 (bd, 1H), 3.30 (m, 1H), 3.77 (m, 1H), 4.18 (m, 1H), 4.21 (d, 1H), 4.37 (d, 1H), 4.86 (m, 1H), 5.17 (m, 1H), 6.01 (d, 1H), 6.23 (d, 1H).

EXAMPLES

Example 1

1(S); 3(R) -Dihydroxy-20(R)-(1.4-dihydroxy-4-ethyl-2-hexyn-1-yl) -9,10-seco-pregna-5(Z), 7(E), 10(19)-triene; isomer A (Compound 101)

Method: General Procedure 11.
Starting material IIIA: Compound 30.
Chromatography eluant: Ethyl acetate.
NMR: δ=0.56 (s, 3H), 1.03 (t, 6H), 1.03 (d, 3H), 1.20–2.07 (m, 22H), 2.32 (dd, 1H), 2.60 (dd, 1H), 2.84 (m, 1H), 4.23 (m, 1H), 4.44 (m, 1H), 4.65 (m, 1H), 5.00 (m, 1H), 5.33 (m, 1H), 6.02 (d, 1H), 6.38 (d, 1H).

Example 2

1(S). 3(R) -Dihydroxy-20(R)-(1.4-dihydroxy-4-ethyl-2-hexyn-1-yl)-9.10.seco-pregna-5(Z).7(E).10(19)-triene; isomer B (Compound 102)

Method: General Procedure 11.
Starting material IIIB: Compound 31.
Chromatography eluant: Ethyl acetate.
NMR: δ=0.57 (s, 3H), 0.99 (d, 3H), 1.05 (t, 6H), 1.15–2.15 (m, 22H), 2.32 (dd, 1H), 2.60 (dd, 1H), 2.83 (m, 1H), 4.24 (m, 1H), 4.44 (m, 1H), 4.66 (m, 1H), 5.00 (m, 1H), 5.33 (m, 1H), 6.02 (d, 1H), 6.37 (d, 1H).

Example 3

1(S);3(R)-Dihydroxy-20(R)-(1-acetoxy-4-ethyl-4-hydroxy-2-hexyn-1-yl)-9,10-seco-pregna-5(Z),7(E)-10(19)-triene; isomer A (Compound 103)

Method: General Procedure 11.
Starting material IIIA: Compound 32.
Chromatography eluant: Ethyl acetate.
NMR: δ=0.53 (s, 3H), 1.00 (t, 6H), 1.07 (d, 3H), 1.10–2.10 (m, 21H), 2.07 (s, 3H), 2.30 (dd, 1H), 2,58 (dd, 1H), 2.82 (m, 1H), 4.22 (m, 1H), 4.42 (m, 1H), 4.98 (m, 1H), 5.32 (m, 1H), 5.38 (d, 1H), 6.01 (d, 1H), 6.35 (d, 1H).

Example 4

1(S),3(R)-Dihydroxy-20(R)-(4-ethyl-4-hydroxy-2-phenoxythiocarbonyloxy-2-hexyn-1-yl)-9,10-seco-pregna-5(Z),7(E),10(19)-triene; isomer A (Compound 104)

Method: General Procedure 11.
Starting material IIIA: Compound 33.
Chromatography eluant: Ethyl acetate.
NMR: δ=0.58 (s, 3H), 1.04 (t, 6H), 1.15 (d, 3H), 1.20–2.10 (m, 21H), 2.31 (dd, 1H), 2.59 (bd, 1H), 2.84 (bd, 1H), 4.23 (m, 1H), 4.43 (m, 1H), 5.00 (m, 1H), 5.33 (m, 1H), 5.74 (d, 1H), 6.03 (d, 1H), 6.37 (d, 1H), 7.08 (m, 2H), 7.30 (m, 1H), 7.43 (m, 2H).

Example 5

1(S),3(R)-Dihydroxy-20(R)-(1,5-dihydroxy-5-methyl-2-hexyn-1-yl)-9,10-seco-pregna-5(Z),7(E),10(19)-triene: isomer A (Compound 105)

Method: General Procedure 11.
Starting material IIIA: Compound 34.
Chromatography eluant: 25% to 0% hexane in ethyl acetate.
NMR: δ=0.57 (s, 3H), 1.04 (d, 3H), 1.25 (s, 6H), 1.20–2.10 (m, 14H), 2.28 (dd, 1H), 2.33 (m, 2H), 2.51 (dd, 1H), 2.86 (dd, 1H), 3.44 (s, 1H), 3.63 (d, 1H), 3.88 (d, 1H), 3.92 (d, 1H), 4.16 (m, 1H), 4.40 (m, 1H), 4.55 (m, 1H), 4.87 (m, 1H), 5.32 (m, 1H), 6.09 (d, 1H), 6.29 (d, 1H).

Example 6

1(S),3(R) -Dihydroxy-20.(R)-(1,5-dihydroxy-5-ethyl-2-heptyn-1-yl]-9,10-seco-pregna-5(Z),7(E), 10(19 )-triene; isomer A (Compound 106)

Method: General Procedure 11.
Starting material IIIA: Compound 35.
Chromatography eluant: 25% to 0% hexane in ethyl acetate.

NMR: δ=0.55 (s, 3H), 0.89 (t, 6H), 1.02 (d, 3H), 1.15–2.40 (m, 22H), 2.31 (dd, 1H), 2.37 (m, 2H), 2.58 (dd, 1H), 2.83 (dd, 1H), 4.22 (m, 1H), 4.43 (m, 1H), 4.59 (m, 1H), 4.99 (m, 1H), 5.33 (m, 1H), 6.03 (d, 1H), 6.36 (d, 1H).

Example 7

1(S),3(R)-Dihydroxy-20(R)-(1,5-dihydroxy-5-ethyl-2-heptyn-1-yl)-9,10-seco-pregna-5(Z); 7(E),10(19)-triene; isomer B (Compound 107)

Method: General Procedure 11.
Starting material IIIB: Compound 36.
Chromatography eluant: 25% to 0% hexane in ethyl acetate.
NMR: δ=0.57 (s, 3H), 0.91 (t, 6H), 0.99 (d, 3H) 1.15–2.45 (m, 23H), 2.41 (m, 2H), 2.60 (dd, 1H), 2.83 (dd, 1H), 4.23 (m, 1H), 4.44 (m, 1H), 4.65 (m, 1H), 5.00 (m, 1H), 5.33 (m, 1H), 6.02 (d, 1H), 6.37 (d, 1H).

Example 8

1(S),3(R)-Dihydroxy-20(R)-(5-ethyl-5-hydroxy-1-methoxy-2-heptyn-1-yl)-9,10-seco-pregna-5(Z),7(E),10f19)-triene; isomer A (Compound 108)

Method: General Procedure 12.
Starting material IIIA: Compound 37.
NMR: δ=0.55 (s, 3H), 0.91 (t, 6H), 1.02 (d, 3H), 1.20–2.10 (m, 21H), 2.29 (dd, 1H), 2.40 (m, 2H), 2.59 (dd, 1H), 2.84 (m 1H), 3.35 (s, 3H), 4.11 (m, 1H), 4.22 (m, 1H), 4.43 (m, 1H), 5.00 (m, 1H), 5.33 (m, 1H), 6.02 (d, 1H), 6.37 (d, 1H).

Example 9

1(S),3(R)-Dihydroxy-20(R)-(1-ethoxy,5-ethyl-5-hydroxy-2-heptyn-1-yl)-9,10-seco-pregna-5(Z),7(E),10(19)-triene; isomer A (Compound 109)

Method: General Procedure 12.
Starting material IIIA: Compound 38.
NMR: δ=0.55 (s, 3H), 0.90 (t, 6H), 1.02 (d, 3H), 1.20 (t, 3H), 1.15–2.10 (m, 21H), 2.31 (dd, 1H), 2.39 (m, 2H), 2.59 (dd, 1H), 2.83 (dd, 1H), 3.31 (m, 1H), 3.75 (m, 1H, 4.17 (m, 1H), 4.22 (m, 1H), 4.43 (m, 1H), 5.00 (m, 1H), 5.33 (m, 1H), 6.02 (d, 1H), 6.37 (d, 1H).

Example 10

1(S),3(R)-Dihydroxy-20(R)-(1-butoxy-5-ethyl-5,hydroxy-2-heptyn-1-yl)-9,10-seco-pregna-5(Z),7(E),10(19)-triene; isomer A ( Compound 110)

Method: General Procedure 12.
Starting material IIIA: Compound 39.
NMR: δ=0.54 (s, 3H), 0.90 (t, 6H), 0.92 (t, 3H) 1.01 (d, 3H), 1.20–2.10 (m, 25H), 2.31 (dd, 1H), 2.39 (m, 2H), 2.60 (dd, 1H), 2.84 (dd, 1H), 3.24 (m, 1H), 3.68 (m, 1H, 4.13 (m, 1H), 4.23 (m, 1H), 4.43 (m, 1H), 5.00 (m, 1H), 5.33 (m, 1H), 6.02 (d, 1H), 6.38 (d, 1H).

Example 11

1(S),3(R)-Dihydroxy-20(R)-(5-ethyl-5-hydroxy-1-(3-methylbutyloxy)-2-heptyn-1-yl)-9,10-seco-pregna-5(Z),7(E),10(19)-triene; isomer A (Compound 111)

Method: General Procedure 11.
Starting material ILIA: Compound 40.
Chromatography eluant: 50% to 0% hexane in ethyl acetate.
NMR: δ=0.54 (s, 3H), 0.90 (t, 6H), 0.91 (d, 6H) 1.01 (d, 3H), 1.20–2.05 (m, 24H), 2.31 (dd, 1H), 2.39 (m, 2H), 2.59 (dd, 1H), 2.84 (dd, 1H), 3.25 (m, 1H), 3.71 (m, 1H, 4.13 (m, 1H), 4.23 (m, 1H), 4.43 (m, 1H), 5.00 (m, 1H), 5.33 (m, 1H), 6.02 (d, 1H), 6.38 (d, 1H).

Example 12

1(S),3(R)-Dihydroxy-20(R)-(1-benzyloxy-5-ethyl-5-hydroxy-2-heptyn-1-yl)-9,10-seco-pregna-5(Z), 7(E),10(19)-triene; isomer A (Compound 112)

Method: General Procedure 11.
Starting material IIIA: Compound 41.
Chromatography eluant: 50% to 0% hexane in ethyl acetate.
NMR: δ=0.54 (s, 3H), 0.91 (t, 6H) 1.06 (d, 3H), 1.15–2.05 (m, 21H), 2.30 (dd, 1H), 2.42 (m, 2H), 2.57 (dd, 1H), 2.81 (bd, 1H), 4.21 (m, 1H), 4,29 (m, 1H), 4,41 (m, 1H), 4,41 (d, 1H), 4.77 (d, 1H), 4.99 (m, 1H), 5,32 (m, 1H), 6.01 (d, 1H), 6.36 (d, 1H), 7.23–7.40 (m, 5H).

Example 13

1(S),3(R)-Dihydroxy-20(R)-(1-acetoxy-5-ethyl-5-hydroxy-2-heptyn-1-yl)-9,10-seco-pregna-5(Z),7(E).10(19)-triene; isomer A (Compound 113)

Method: General Procedure 11.
Starting material IIIA: Compound 42.
Chromatography eluant: 25% to 0% hexane in ethyl acetate.
NMR: δ=0.55 (s, 3H), 0.88 (t, 6H), 1.08 (d, 3H), 2.08 (s, 3H), 1.05–2.10 (m, 21H), 2.33 (dd, 1H), 2.36 (m, 2H), 2.59 (dd, 1H), 2.83 (dd, 1H), 4.22 (m, 1H), 4.43 (m, 1H), 4.99 (m, 1H), 5.33 (m, 1H), 5.34 (m, 1H), 6.02 (d, 1H), 6.36 (d, 1H).

Example 14

1(S),3(R)-Dihydroxy-20(R)-(5-ethyl-5-hydroxy-1-pivaloyloxy-2-heptyn-1-yl)-9,10-seco-pregna-5(Z),7(E),10(19)-triene; isomer A (Compound 114)

Method: General Procedure 11.
Starting material IIIA: Compound 43.
Chromatography eluant: 25% to 0% hexane in ethyl acetate.
NMR: δ=0.56 (s, 3H), 0.87 (m, 6H), 1.11 (d, 3H), 1.22 (s, 9H), 1.05–2.10 (m, 21H), 2.32 (dd, 1H), 2.34 (m, 2H), 2.59 (dd, 1H), 2.83 (dd, 1H), 4.23 (m, 1H), 4.42 (m, 1H), 4.99 (m, 1H), 5.31 (m, 1H), 5.33 (m, 1H), 6.02 (d, 1H), 6.36 (d, 1H).

Example 15

1(S),3(R)-Dihydroxy-20(R)-(1,6-dihydroxy-6-methyl-2-heptyn-1-yl)-9,10-seco-pregna-5(Z),7(E),10(19)-triene; isomer A (Compound 115)

Method: General Procedure 11.
Starting material IIIA: Compound 44.
Chromatography eluant: 25% to 0% hexane in ethyl acetate.
NMR: δ=0.56 (s, 3H), 1.01 (d, 3H), 1.17 (s, 6H), 1.25–2.10 (m, 16H), 2.28 (m, 3H), 2.50 (dd, 1H), 2.87 (dd, 1H), 3.36 (bs, 1H), 3.72 (m, 1H), 3.87 (d, 1H), 3.94 (d, 1H), 4,17 (m, 1H), 4.40 (m, 1H), 4.51 (m, 1H), 4.87 (m, 1H), 5.32 (m, 1H), 6.09 (d, 1H), 6.29 (d, 1H).

Example 16

1(S),3(R)-Dihydroxy-20(R)-(1.6-dihydroxy-6-methyl-2-heptyn-1-yl)-9,10-secopregna-5(Z),7(E)10(19)-triene; isomer B (Compound 116)

Method: General Procedure 11.
Starting material IIIB: Compound 45.

Chromatography eluant: 25% to 0% hexane in ethyl acetate.

NMR: δ=0.58 (s, 3H), 0.98 (d, 3H), 1.18 (s, 6H), 1.15–2.10 (m, 16H), 2.31 (m, 3H), 2.50 (dd, 1H), 2.86 (dd, 1H), 3.32 (s, 1H), 3.66 (d, 1H), 3.91 (d, 1H), 4.01 (d, 1H), 4.16 (m, 1H), 4.40 (m, 1H), 4.57 (m, 1H), 4.87 (m, 1H), 5.32 (m, 1H), 6.10 (d, 1H), 6.29 (d, 1H).

Example 17

1(S), 3( R )-Dihydroxy-20( R).(1.6-dihydroxy-6-ethyl-2-octyn-1-yl)-9,10-seco-pregna-5(Z),7(E),10(19)triene; isomer A (Compound 117)

Method: General Procedure 11.
Starting material IIIA: Compound 46.
Chromatography eluant: 25% to 0% hexane in ethyl acetate.

NMR: δ=0.56 (s, 3H), 0.84 (t, 6H), 1.01 (d, 3H), 1.45 (q, 4H), 1.25–2.10 (m, 16H), 2.23 (m, 2H), 2.29 (dd, 1H), 2.51 (dd, 1H), 2.86 (dd, 1H), 3.09 (bs, 1H), 3.71 (bs, 1H), 3.87 (d, 1H), 3.94 (bd, 1H), 4,17 (m, 1H), 4.40 (m, 1H), 4.50 (m, 1H), 4.87 (m, 1H), 5.32 (m, 1H), 6.09 (d, 1H), 6.29 (d, 1H).

Example 18

1(S),3(R)-Dihydroxy-20(R)-(1.6-dihydroxy-6-ethyl-2-octyn-1-yl)-9,10-seco-pregna-5(Z),7(E),10(19)-triene; isomer B (Compound 118)

Method: General Procedure 11.
Starting material IIIB: Compound 47.
Chromatography eluant: 25% to 0% hexane in ethyl acetate.

NMR: δ=0.58 (s, 3H), 0.85 (t, 6H), 0.98 (d, 3H), 1.46 (q, 4H), 1.25–2.10 (m, 16H), 2.28 (m, 3H), 2.50 (dd, 1H), 2.86 (dd, 1H), 3.07 (s, 1H), 3.66 (d, 1H), 3.91 (d, 1H), 4.02 (d, 1H), 4,17 (m, 1H), 4.40 (m, 1H), 4.57 (m, 1H), 4.86 (m, 1H), 5.32 (m, 1H), 6.09 (d, 1H), 6.29 (d, 1H).

Example 19

1(S),3(R)-Dihydroxy-20(R)-(1,7-dihydroxy-7-ethyl-2-nonyn-1-yl)-9,10-seco-pregna-5(Z),7(E),10(19)-triene; isomer A (Compound 119)

Method: General Procedure 11.
Starting material IIIA: Compound 48.
Chromatography eluant: 25% to 0% hexane in ethyl acetate.

NMR: δ=0.55 (s, 3H), 0.86 (t, 6H), 1.03 (d, 3H), 1.47 (q, 4H), 1.10–2.10 (m, 22H), 2.23 (m, 2H), 2,31 (dd, 1H), 2.60 (bd, 1H), 2.84 (bd, 1H), 4.23 (m, 1H), 4.43 (m, 1H), 4.58 (m, 1H), 5.00 (m, 1H), 5.33 (m, 1H), 6.02 (d, 1H), 6.37 (d, 1H).

Example 20

1(S),3(R)-Dihydroxy,20(R)-(1,7-dihydroxy-7-ethyl-2-nonyn-1-yl)-9,10-seco-pregna-5(Z),7(E),10(19)-triene; isomer B (Compound 120)

Method: General Procedure 11.
Starting material IIIB: Compound 49.
Chromatography eluant: 25% to 0% hexane in ethyl acetate.

NMR: δ=0.58 (s, 3H), 0.86 (t, 6H), 0.99 (d, 3H), 1.45 (q, 4H), 1.35–2.10 (m, 18H), 2.22 (m, 2H), 2.28 (dd, 1H), 2.50 (dd, 1H), 2.85 (m, 1H), 2.91 (s, 1H), 3.66 (d, 1H), 3.91 (d, 1H), 4.02 (d, 1H), 4.16 (m, 1H), 4.40 (m, 1H), 4.60 (m, 1H), 4.87 (m, 1H), 5.32 (m, 1H), 6.10 (d, 1H), 6.29 (d, 1H).

Example 21

1(S),3(R) -Dihydroxy-20(R)-(1-methoxy-4-hydroxy-4-ethyl-2-hexyn-1-yl)-9,10-seco-pregna-5(Z),7(E),10(19)-triene; isomer A (Compound 130)

Method: General Procedure 11.
Starting material IIIA: Compound 52.
Chromatography eluant: Ethyl acetate.

NMR: δ=0.55 (s, 3H), 1.02 (d, 3H), 1.05 (t, 6H), 1.68 (m, 4H), 1.20–2.10 (m, 17H), 2.32 (dd, 1H), 2.60 (dd, 1H), 2.84 (m, 1H), 3.36 (s, 3H), 4.16 (d, 1H), 4.23 (m, 1H), 4.43 (m, 1H), 5.00 (m, 1H), 5.33 (m, 1H), 6.02 (d, 1H), 6.38 (d, 1H).

Example 22

1(S),3(R)-Dihydroxy-20(R)-(1-ethoxy-4-hydroxy-4-ethyl-2-hexyn-1-yl)-9,10-seco-pregna-5(Z),7(E),10(19)-triene; isomer A (Compound 135)

Method: General Procedure 11.
Starting material IIIA: Compound 53.
Chromatography eluant: Ethyl acetate.

NMR: δ=0.55 (s, 3H), 1.03 (d, 3H), 1.04 (t, 6H), 1.20 (t, 3H), 1.12–2.20 (m, 21H), 2.31 (dd, 1H), 2.59 (bd, 1H), 2.83 (m, 1H), 3.31 (m, 1H), 3.76 (m, 1H), 4.22 (m, 2H), 4.42 (m, 1H), 5.00 (m, 1H), 5.33 (m, 1H), 6.02 (d, 1H), 6.38 (d, 1H).

Example 23

Capsules containing Compound 109

Compound 109 was dissolved in arachis oil to a final concentration of 1 μg of Compound 109/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of Compound 109 in oil solution, such that each capsule contained 0.1 μg of Compound 109.

Example 24

Dermatological Cream Containing Compound 109

In 1 g almond oil was dissolved 0.05 mg of Compound 109. To this solution was added 40 g of mineral oil and 20 g of self-emulsifying beeswax. The mixture was heated to liquify. After the addition of 40 ml hot water, the mixture was mixed well. The resulting cream contains approximately 0.5 μg of Compound 109 per gram of cream.

What we claim is:

1. A compound of the formula I

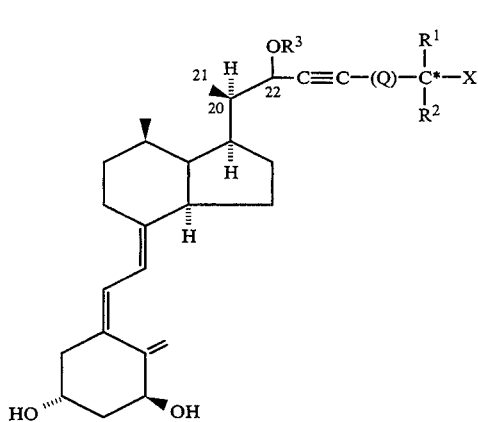

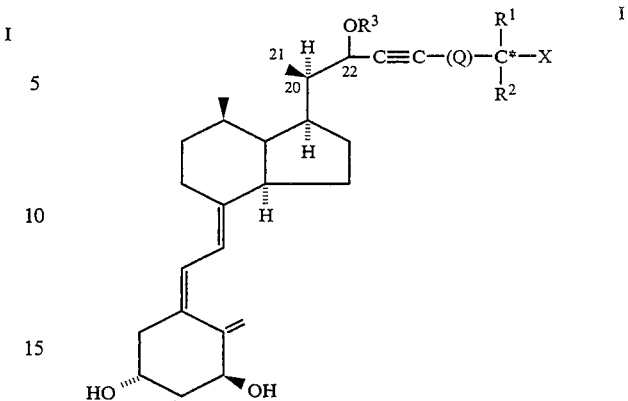

in which formula X is hydrogen or hydroxy; $R^1$ and $R^2$ which may be the same or different, stand for hydrogen or a $C_1$–$C_6$ hydrocarbyl radical; or $R^1$ and $R^2$ taken together with the carbon atom (starred in formula I) bearing the group X, can form a $C_3$–$C_8$ carbocyclic ring; $R^3$ stands for hydrogen or a $C_1$–$C_{10}$ hydrocarbyl radical or for $YR^4$ in which Y stands for the radicals —CO—, —CO—O—, —CO—S—, —CS—, —CS—O—, —CS—S—, —SO— or —SO$_2$—, and $R^4$ stands for hydrogen or a $C_1$–$C_{10}$ hydrocarbyl radical; Q is a single bond or a $C_1$–$C_8$ hydrocarbylene diradical; $R^1$, $R^2$, $R^3$ and/or Q may be optionally substituted with one or more deuterium or fluorine atoms.

2. A diastereoisomer of a compound according to claim 1, in pure form; or a mixture of diastereoisomers of a compound according to claim 1.

3. A compound according to claim 1 which is

1(S),3(R)-Dihydroxy-20(R)-(1,5-dihydroxy-5-ethyl-2-heptyn-1-yl)-9,10-seco-pregna-5(Z),7(E),10(19)-triene; isomer A, 1(S),3(R)-Dihydroxy-20(R)-(5-ethyl-5-hydroxy-1-methoxy-2-heptyn-1-yl)-9,10-seco-pregna-5(Z),7(E),10(19)-triene; isomer A, 1(S),3(R)-Dihydroxy-20(R)-(1-ethoxy-5-ethyl-5-hydroxy-2-heptyn-1-yl)-9,10-seco-pregna-5(Z),7(E),10(19)-triene; isomer A, 1(S),3(R)-Dihydroxy-20(R)-(1-methoxy-4-hydroxy-4-ethyl-2-hexyn-1-yl)-9,10-seco-pregna-5(Z),7(E),10(19)-triene; isomer A, or 1(S),3(R)-Dihydroxy-20(R)-(1-ethoxy-4-hydroxy-4-ethyl-2-hexyn-1-yl)-9,10-seco-pregna-5(Z),7(E),10(19)-triene; isomer A.

4. A method for producing a compound of formula I:

in which formula X is hydrogen or hydroxy; $R^1$ and $R^2$ which may be the same or different, stand for hydrogen or a $C_1$–$C_6$ hydrocarbyl radical; or $R^1$ and $R^2$ taken together with the carbon atom (starred in formula I) bearing the group X, can form a $C_3$–$C_8$ carbocyclic ring; $R^3$ stands for hydrogen or a $C_1$–$C_{10}$ hydrocarbyl radical or for $YR^4$ in which Y stands for the radicals —CO—, —CO—O—, —CO—S, —CS—, —CS—O—, —CS—S—, —SO— or —S0$_2$—, and $R^4$ stands for hydrogen or a $C_1$–$C_{10}$ hydrocarbyl radical; Q is a single bond or a $C_1$–$C_8$ hydrocarbylene diradical; $R^1$, $R^2$, $R^3$ and/or Q may be optionally substituted with one or more deuterium or fluorine atoms, in which a) 1(S),3(R)-bis-(tert-butyldimethylsilyloxy)-20(R)-formyl-9,10-seco-pregna-5(E),7(E),10(19)-triene is reacted with the anion R−, derived from the side chain building block, RH, of formula V V: RH, R being

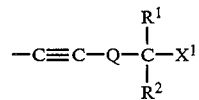

which $X^1$ is H, OH or $OR^5$, $R^5$ being an alcohol protective group, and $R^1$, $R^2$ and Q have the above meanings with a suitable base, to form a mixture of two C-22-epimers IIA and IIB, in which $R^3$ stands for H, and R have the above meaning

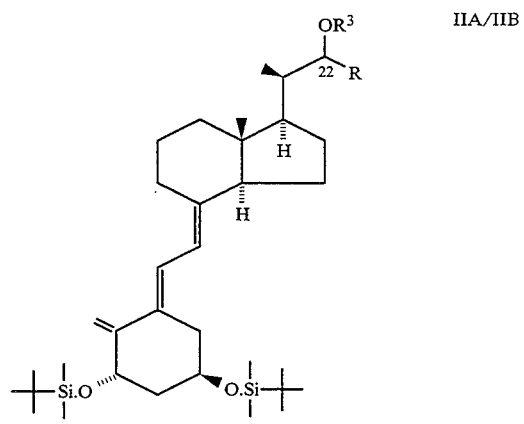

which epimers are separated;

b) a compound of formula IIA or IIB of step a), where $R^3$=H, is optionally alkylated to the corresponding compound IIA or IIB, in which $R^3$ is $C_1$-$C_{10}$ hydrocarbyl or optionally acylated to the corresponding compound IIA or IIB, where $R^3$=$YR^4$, Y and $R^4$ having the above meanings;

c) a compound of formula IIA or IIB of step a) or step b) is isomerized to the corresponding compound IIIA or IIIB by means of UV-light in the presence of a triplet sensitizer

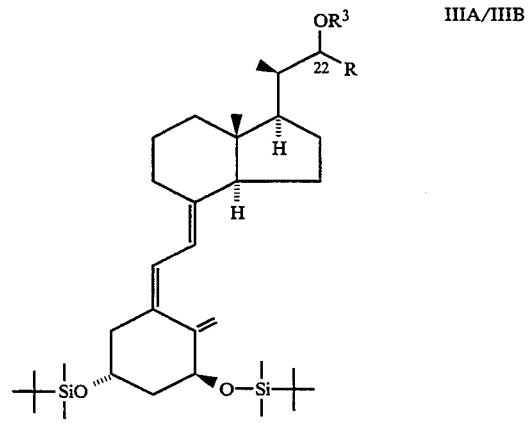

IIIA/IIIB in which R and $R^3$ have the above meanings;

d) a compound of formula IIIA or IIIB is deprotected to the corresponding compound of the general formula I.

5. A method according to claim 4 in which steps b) and c) are performed in the reverse order.

6. A pharmaceutical composition containing an effective amount of one or more of the compounds of claim 1, together with pharmaceutically acceptable, non-toxic carriers.

7. A pharmaceutical composition according to claim 6 in dosage unit form.

8. A dosage unit according to claim 7 containing from 0.1 ppm to 0.1% by weight of the dosage unit of a compound of formula I.

* * * * *

UNITED STATES PATENT AND TRADEMARK OFFICE
CERTIFICATE OF CORRECTION

PATENT NO. : 5,446,034
DATED : August 29, 1995
INVENTOR(S) : Bretting et al.

Page 1 of 8

It is certified that error appears in the above-indentified patent and that said Letters Patent is hereby corrected as shown below:

Column 1, line 26-41, change

"
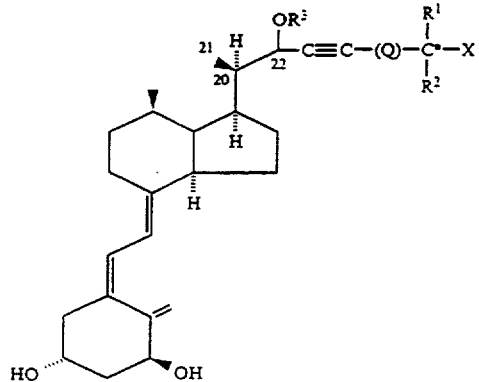

to

--
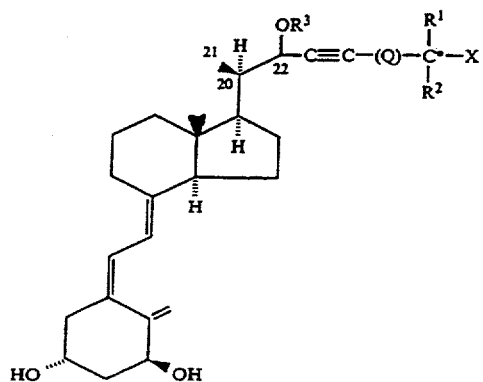

--;

UNITED STATES PATENT AND TRADEMARK OFFICE
CERTIFICATE OF CORRECTION

PATENT NO. : 5,446,034
DATED : August 29, 1995
INVENTOR(S) : Bretting et al.

It is certified that error appears in the above-indentified patent and that said Letters Patent is hereby corrected as shown below:

Column 2, line 20, change "Groups", both occurrences, to --groups--;

Column 2, line 35, change "Graft" to --graft--;

Column 3, line 15, change "Blochem." to --Biochem.--;

Column 5, following Scheme 1 in the definition of $R^5$, change "(loweraklyl)" to --(loweralkyl)--;

Column 9, line 60, change "RH = H-C ≡ C-Q-C(R1)(R2)OR$^5$" to --RH = H-C ≡ C-Q-C($R^1$)($R^2$)$OR^5$--;

Column 10, line 29, change "and/IB" to --and IIB--;

Column 11, line 26, change "alkylation" to --acylation--;

Column 17, line 8, change "General Procedures - Preparations" to --General Procedures, Preparations--;

UNITED STATES PATENT AND TRADEMARK OFFICE
CERTIFICATE OF CORRECTION

PATENT NO. : 5,446,034

DATED : August 29, 1995

INVENTOR(S) : BRETTING et al

It is certified that error appears in the above-identified patent and that said Letters Patent is hereby corrected as shown below:

Column 5-6, change formula III A/III B from

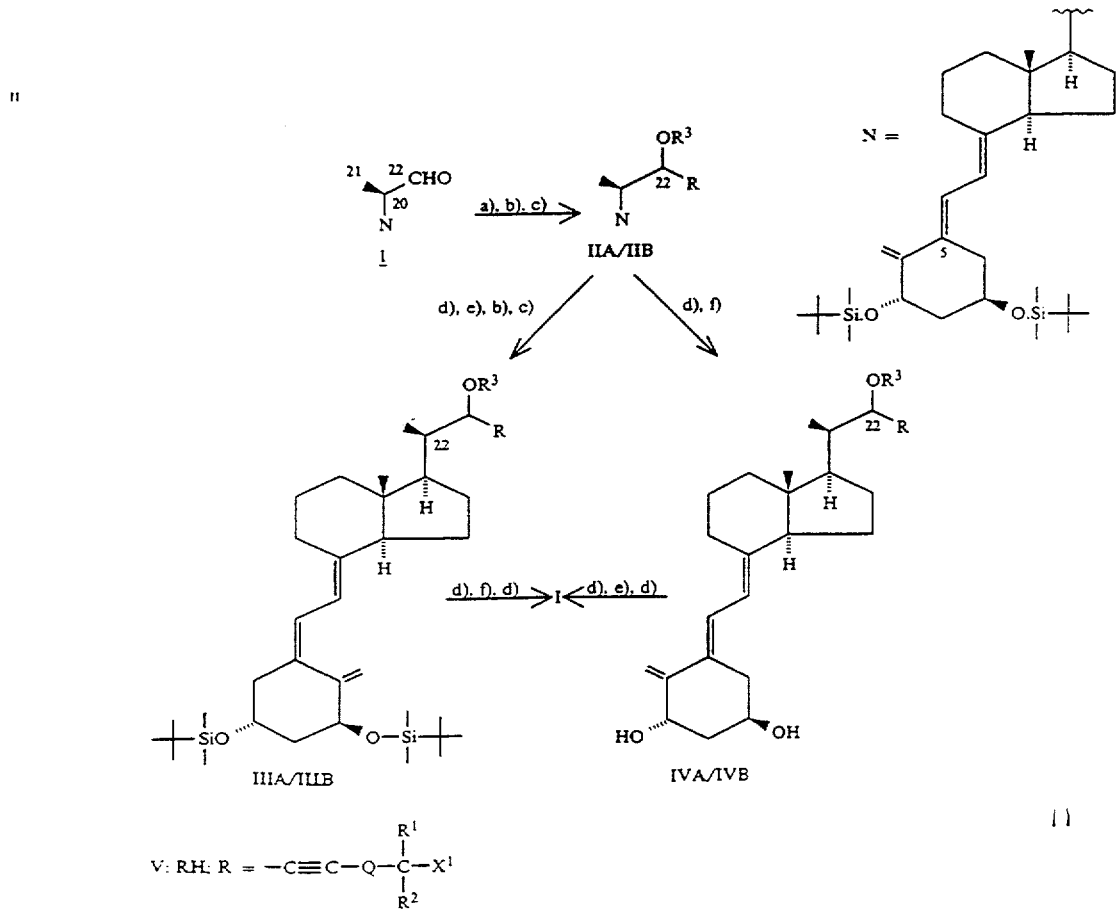

UNITED STATES PATENT AND TRADEMARK OFFICE
CERTIFICATE OF CORRECTION

PATENT NO. : 5,446,034

DATED : August 29, 1995

INVENTOR(S) : BRETTING et al

Page 4 of 8

It is certified that error appears in the above-identified patent and that said Letters Patent is hereby corrected as shown below:

to

--

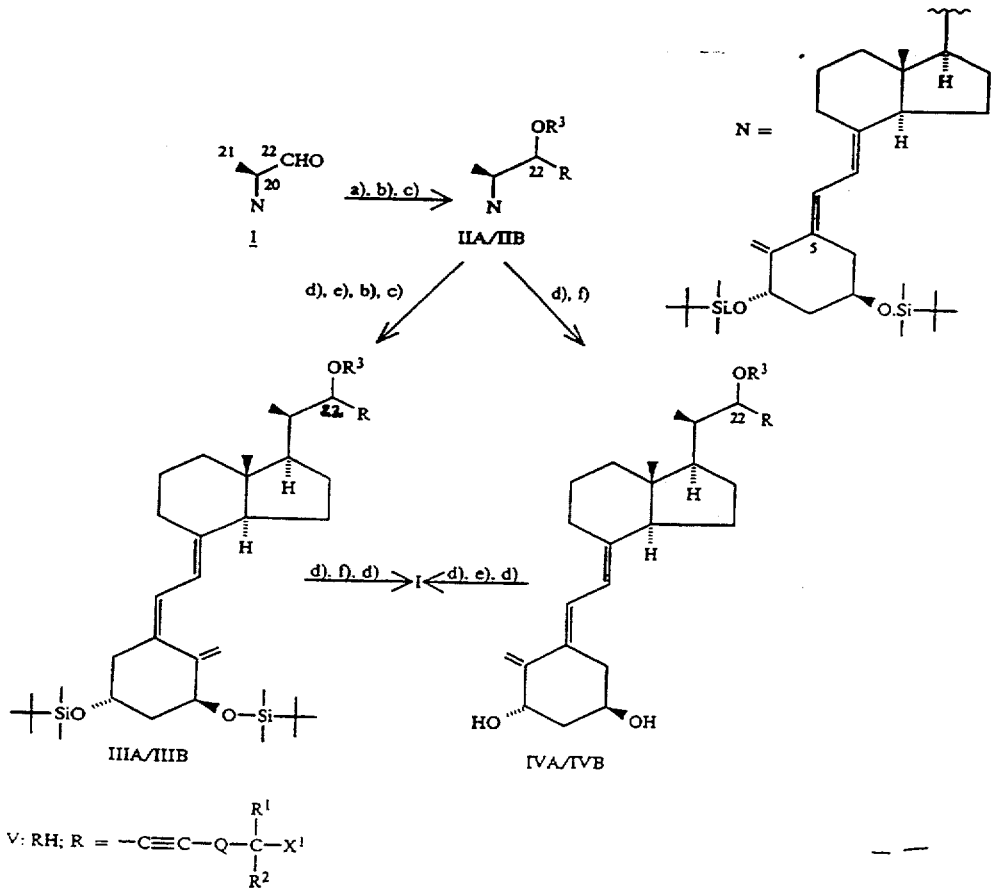

--

UNITED STATES PATENT AND TRADEMARK OFFICE
CERTIFICATE OF CORRECTION

PATENT NO. : 5,446,034
DATED : August 29, 1995
INVENTOR(S) : Bretting et al.

It is certified that error appears in the above-indentified patent and that said Letters Patent is hereby corrected as shown below:

Column 17, line 62, change "oroanometallic" to --organometallic--;

Column 18, line 43, change "Vacuo" to --vacuo--;

Column 18, line 47, change "Procedures" to --Procedure--;

Column 19, line 45, delete "General" and insert --.--;

Column 21, line 9, change "(g, 4H)" to --(q, 4H)--;

Column 21, line 40, following "in" insert --vacuo.--;

Column 21, line 41, change "4" to --6--;

Column 23, line 58, change "108" to --10%--;

Column 25, line 16, change "(4, 3H)" to --(d, 3H)--;

Column 27, line 12, change "6-0.05" to --$\delta = 0.05$--;

Column 28, line 33, change "6-0.05" to --$\delta = 0.05$--;

Column 31, line 24, change "10 f 19" to --10 (19)--;

Column 31, line 46, change "(1-butoxy-5-ethyl-5,hy-" to --(1-butoxy-5-ethyl-5-hy--;

UNITED STATES PATENT AND TRADEMARK OFFICE
CERTIFICATE OF CORRECTION

PATENT NO. : 5,446,034
DATED : August 29, 1995
INVENTOR(S) : Bretting et al.

It is certified that error appears in the above-indentified patent and that said Letters Patent is hereby corrected as shown below:

Column 31, line 34, change "(1-ethoxy, 5-ethyl-5-" to --(1-ethoxy-5-ethyl-5- --;

Column 31, line 63, change "ILIA" to --III--;

Column 35, lines 1-19, change

"
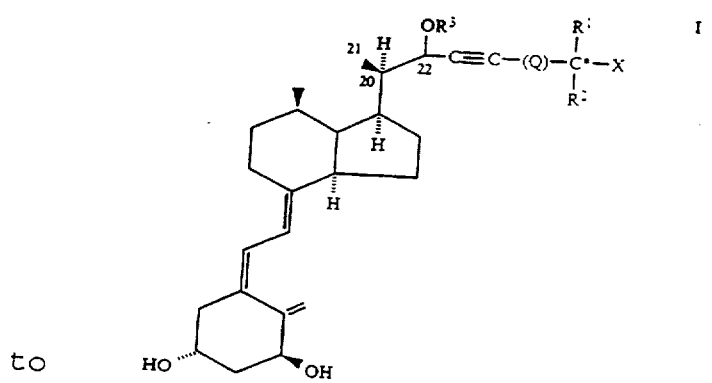
to
"

UNITED STATES PATENT AND TRADEMARK OFFICE
CERTIFICATE OF CORRECTION

PATENT NO. : 5,446,034
DATED : August 29, 1995
INVENTOR(S) : Bretting et al.

It is certified that error appears in the above-indentified patent and that said Letters Patent is hereby corrected as shown below:

"

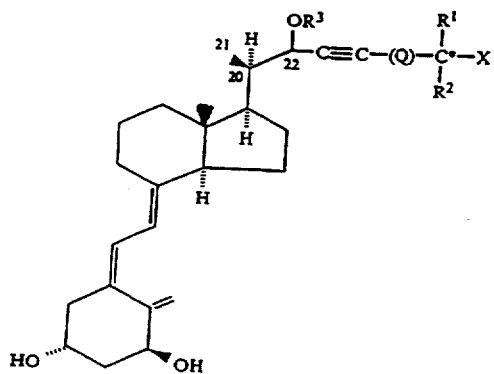

Column 36, line 1-19, change

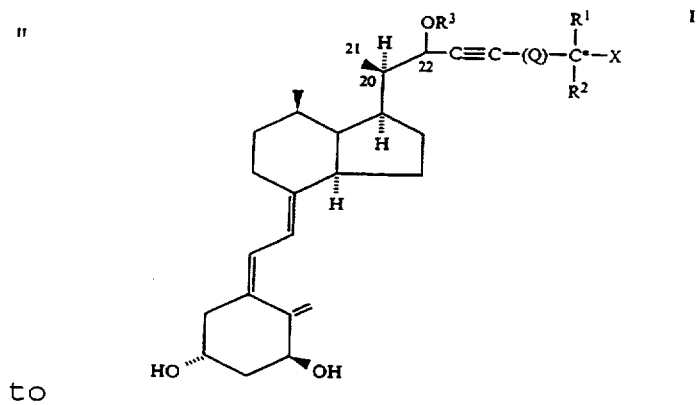

to "

UNITED STATES PATENT AND TRADEMARK OFFICE
CERTIFICATE OF CORRECTION

PATENT NO. : 5,446,034      Page 8 of 8
DATED : August 29, 1995
INVENTOR(S) : Bretting et al.

It is certified that error appears in the above-indentified patent and that said Letters Patent is hereby corrected as shown below:

- -

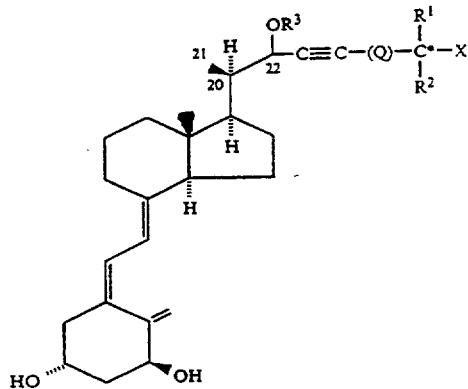

- - ;

Signed and Sealed this

Twenty-first Day of May, 1996

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO.   : 5,446,034

DATED        : August 29, 1995

INVENTOR(S)  : BRETTING et al

It is certified that error appears in the above-identified patent and that said Letters Patent is hereby corrected as shown below:

On the title page: Item [73] should read

```
    -- Leo Pharmaceutical Products Ltd. A/S
       (Løvens kemiske Fabrik Produktionsaktieselskab)
                                      Ballerup, Denmark --.
```

Signed and Sealed this

Twelfth Day of November, 1996

Attest:

BRUCE LEHMAN

Attesting Officer

Commissioner of Patents and Trademarks